US012734307B2

(12) United States Patent
Hee-Hanson et al.

(10) Patent No.: US 12,734,307 B2
(45) Date of Patent: Sep. 15, 2026

(54) MEDICAMENT DELIVERY DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB); Haiming Wu, Weston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 19/064,379

(22) Filed: Feb. 26, 2025

(65) Prior Publication Data

US 2026/0249018 A1 Aug. 27, 2026

(51) Int. Cl.
*A61M 5/32* (2006.01)
*A61M 5/315* (2006.01)

(52) U.S. Cl.
CPC ...... *A61M 5/3202* (2013.01); *A61M 5/31501* (2013.01)

(58) Field of Classification Search
CPC ............ A61M 5/3202; A61M 5/31501; A61M 5/315; A61M 5/32; A61M 2005/31508
See application file for complete search history.

(56) References Cited

U.S. PATENT DOCUMENTS

| | | | |
|---|---|---|---|
| 2,522,961 | A | 9/1950 | William |
| 2,633,267 | A | 3/1953 | Lebus |
| 3,886,513 | A | 5/1975 | Smith et al. |

(Continued)

FOREIGN PATENT DOCUMENTS

| | | | |
|---|---|---|---|
| DE | 2626811 | A1 | 12/1976 |
| DE | 3921747 | A1 | 1/1991 |

(Continued)

OTHER PUBLICATIONS

U.S. Appl. No. 19/063,738, Alexander Hee-Hanson, filed Feb. 26, 2025.

(Continued)

*Primary Examiner* — Tasnim Mehjabin Ahmed
(74) *Attorney, Agent, or Firm* — Fish & Richardson P.C.

(57) ABSTRACT

A medicament delivery device is described. The device includes a body comprising a proximal end and a distal end; a needle for injecting medicament; an actuation member moveable relative to the body for actuating the device; a lock ring configured to rotate relative to the body between a first position in which the actuation member is not permitted to move relative to the body, and a second position in which the actuation member is permitted to move relative to the body; and a cap arrangeable in a capped position in which the cap abuts with and conceals the distal end of the body to conceal the needle; wherein when the cap is in the capped position the lock ring is in a first state in which the lock ring is in the first position and is not permitted to rotate towards the second position; and wherein moving the cap in a distal direction away from the distal end of the body along the longitudinal axis away from the capped position causes the lock ring to be in a second state in which the lock ring is permitted to rotate from the first position towards the second position.

20 Claims, 12 Drawing Sheets

(56) References Cited

U.S. PATENT DOCUMENTS

| | | | |
|---|---|---|---|
| 3,993,063 A | 11/1976 | Larrabee | |
| 4,801,295 A | 1/1989 | Spencer | |
| 5,045,062 A | 9/1991 | Henson | |
| 5,176,275 A | 1/1993 | Bowie | |
| 5,328,484 A | 7/1994 | Somers et al. | |
| 5,396,051 A | 3/1995 | Kuhn et al. | |
| 5,478,316 A | 12/1995 | Bitdinger et al. | |
| 5,505,324 A | 4/1996 | Danico | |
| 5,505,706 A | 4/1996 | Maus et al. | |
| 5,536,917 A | 7/1996 | Suppelsa et al. | |
| 5,622,274 A | 4/1997 | Bright | |
| 5,738,658 A | 4/1998 | Maus et al. | |
| 5,984,899 A | 11/1999 | D'Alessio et al. | |
| 6,080,461 A | 6/2000 | Wozniak et al. | |
| 6,394,985 B1 | 5/2002 | Lin | |
| 7,762,981 B2 | 7/2010 | Dacquay et al. | |
| 7,887,506 B1 | 2/2011 | Smolyarov et al. | |
| 7,918,824 B2 | 4/2011 | Bishop et al. | |
| 8,133,198 B2 | 3/2012 | Neer | |
| 8,409,138 B2 | 4/2013 | James et al. | |
| 8,734,394 B2 | 5/2014 | Adams et al. | |
| 9,044,553 B2 | 6/2015 | James et al. | |
| 9,402,957 B2 | 8/2016 | Adams et al. | |
| 9,474,780 B2 | 10/2016 | Bokvist et al. | |
| 9,872,961 B2 | 1/2018 | Fourt et al. | |
| 10,118,001 B2 | 11/2018 | Fourt et al. | |
| 10,314,981 B2 | 6/2019 | Sampson et al. | |
| 10,350,362 B2 | 7/2019 | Dennis, Jr. et al. | |
| 10,363,377 B2 | 7/2019 | Atterbury et al. | |
| 11,298,462 B2 | 4/2022 | Atterbury et al. | |
| 11,331,432 B2 | 5/2022 | Holmqvist et al. | |
| 11,357,820 B2 | 6/2022 | Corvari et al. | |
| 11,369,751 B2 | 6/2022 | Ruan et al. | |
| 11,452,821 B2 | 9/2022 | LaFever et al. | |
| 2002/0055712 A1 | 5/2002 | Neracher | |
| 2004/0039336 A1 | 2/2004 | Amark et al. | |
| 2005/0101919 A1 | 5/2005 | Brunnberg | |
| 2005/0273061 A1 | 12/2005 | Hommann et al. | |
| 2006/0224124 A1 | 10/2006 | Scherer | |
| 2007/0270777 A1 | 11/2007 | Dacquay et al. | |
| 2008/0097311 A1 | 4/2008 | Dacquay et al. | |
| 2008/0097390 A1 | 4/2008 | Dacquay et al. | |
| 2008/0110935 A1 | 5/2008 | Huber et al. | |
| 2008/0269692 A1 | 10/2008 | James et al. | |
| 2009/0036868 A1 | 2/2009 | Pinedjian et al. | |
| 2009/0281496 A1 | 11/2009 | Matusch | |
| 2010/0049125 A1* | 2/2010 | James | A61M 5/2033 604/110 |
| 2010/0211005 A1 | 8/2010 | Edwards et al. | |
| 2011/0034878 A1 | 2/2011 | Radmer et al. | |
| 2011/0054414 A1 | 3/2011 | Shang et al. | |
| 2011/0144594 A1 | 6/2011 | Sund et al. | |
| 2011/0202011 A1 | 8/2011 | Wozencroft | |
| 2011/0319813 A1 | 12/2011 | Kamen et al. | |
| 2011/0319864 A1 | 12/2011 | Beller et al. | |
| 2013/0237921 A1 | 9/2013 | Lannan et al. | |
| 2013/0267897 A1 | 10/2013 | Kemp et al. | |
| 2014/0236076 A1 | 8/2014 | Marshall et al. | |
| 2014/0249483 A1 | 9/2014 | Kiilerich et al. | |
| 2014/0263156 A1 | 9/2014 | Newsom et al. | |
| 2014/0276637 A1 | 9/2014 | Massey, Jr. | |
| 2015/0174325 A1 | 6/2015 | Young et al. | |
| 2015/0246180 A1 | 9/2015 | Fenlon et al. | |
| 2015/0246181 A1 | 9/2015 | Fourt et al. | |
| 2015/0273162 A1 | 10/2015 | Holmqvist | |
| 2016/0001015 A1 | 1/2016 | Kucuk et al. | |
| 2016/0354555 A1 | 12/2016 | Gibson et al. | |
| 2016/0367763 A1 | 12/2016 | Tschirren et al. | |
| 2017/0173264 A1 | 6/2017 | Bendek et al. | |
| 2017/0215699 A1 | 8/2017 | Ouyang et al. | |
| 2017/0216526 A1 | 8/2017 | Brereton et al. | |
| 2017/0224929 A1 | 8/2017 | Sampson et al. | |
| 2017/0246403 A1 | 8/2017 | Cowe et al. | |
| 2017/0354790 A1 | 12/2017 | Atterbury et al. | |
| 2017/0361034 A1 | 12/2017 | Scheller et al. | |
| 2018/0110935 A1 | 4/2018 | Carroll et al. | |
| 2018/0250471 A1 | 9/2018 | Grimoldby et al. | |
| 2018/0339114 A1 | 11/2018 | Wendland et al. | |
| 2019/0030249 A1 | 1/2019 | Gonzalez et al. | |
| 2019/0046735 A1 | 2/2019 | Ingerslev et al. | |
| 2019/0192785 A1 | 6/2019 | Wendland et al. | |
| 2019/0366000 A1 | 12/2019 | Cowe et al. | |
| 2020/0114041 A1 | 4/2020 | Alas et al. | |
| 2020/0121853 A1 | 4/2020 | Dobson et al. | |
| 2020/0139046 A1* | 5/2020 | Jacobsen | A61M 5/31595 |
| 2020/0282144 A1 | 9/2020 | Pearson | |
| 2020/0316314 A1 | 10/2020 | Buri et al. | |
| 2021/0077732 A1 | 3/2021 | Egelhofer | |
| 2021/0196900 A1 | 7/2021 | Apply et al. | |
| 2022/0015429 A1 | 1/2022 | Brown et al. | |
| 2022/0176042 A1 | 6/2022 | Belisle | |
| 2022/0395640 A1 | 12/2022 | Schwartzentruber | |
| 2023/0001099 A1 | 1/2023 | Dunn | |
| 2023/0158249 A1 | 5/2023 | Van Der Beek | |
| 2023/0238105 A1 | 7/2023 | Schneider et al. | |
| 2023/0347074 A1 | 11/2023 | Gavin | |
| 2024/0009397 A1 | 1/2024 | In et al. | |
| 2024/0065940 A1 | 2/2024 | Foucher et al. | |

FOREIGN PATENT DOCUMENTS

| | | |
|---|---|---|
| EP | 3501577 A1 | 6/2019 |
| WO | WO 2002/047746 A1 | 6/2002 |
| WO | WO 2004/058820 A2 | 7/2004 |
| WO | WO 2004/068820 A2 | 8/2004 |
| WO | WO 2005/018629 A1 | 3/2005 |
| WO | WO 2006/003388 A2 | 1/2006 |
| WO | WO 2006/030220 A1 | 3/2006 |
| WO | WO 2011/109205 A2 | 9/2011 |
| WO | WO 2015/001819 A1 | 1/2015 |
| WO | WO 2016/081238 A1 | 5/2016 |
| WO | WO 2018/142167 A1 | 8/2018 |
| WO | WO 2019/074788 A1 | 4/2019 |
| WO | WO 2020/190529 A1 | 9/2020 |

OTHER PUBLICATIONS

U.S. Appl. No. 19/064,323, Alexander Hee-Hanson, filed Feb. 26, 2025.

U.S. Appl. No. 19/064,354, Alexander Hee-Hanson, filed Feb. 26, 2025.

U.S. Appl. No. 19/064,399, Alexander Hee-Hanson, filed Feb. 26, 2025.

Hamers-Casterman et al., "Naturally occurring antibodies devoid of light chains," Nature, Jun. 3, 1993, 363(6428):446-448.

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use requirements and test methods, Part 1: Needle injection systems, ISO 11608 1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 1, 1989, 341(6242):544-546.

U.S. Appl. No. 19/063,738, filed Feb. 26, 2025, Alexander Hee-Hanson.

U.S. Appl. No. 19/064,399, filed Feb. 26, 2025, Alexander Hee-Hanson.

U.S. Appl. No. 19/064,323, filed Feb. 26, 2025, Alexander Hee-Hanson.

U.S. Appl. No. 19/064,354, filed Feb. 26, 2025, Alexander Hee-Hanson.

International Search Report and Written Opinion in International Appln. No. PCT/US2025/044876, mailed on Dec. 22, 2025, 20 pages.

International Search Report and Written Opinion in International Appln. No. PCT/US2025/045033, mailed on Jan. 27, 2026, 10 pages.

(56) References Cited

OTHER PUBLICATIONS

International Search Report and Written Opinion in International Appln. No. PCT/US2026/016343, mailed on May 28, 2026, 14 pages.
International Search Report and Written Opinion in International Appln. No. PCT/US2026/016378, mailed on May 29, 2026, 15 pages.
International Search Report and Written Opinion in International Appln. No. PCT/US2026/016414, mailed on May 28, 2026, 15 pages.

* cited by examiner 10
12
20
11
23
21
22
X 12
17
13
10
20
11
23
21
22
X 200
227
208
242
228
264
265
260
223
201
262
250
217
232
258
216
229
240
268
267
202
254
266

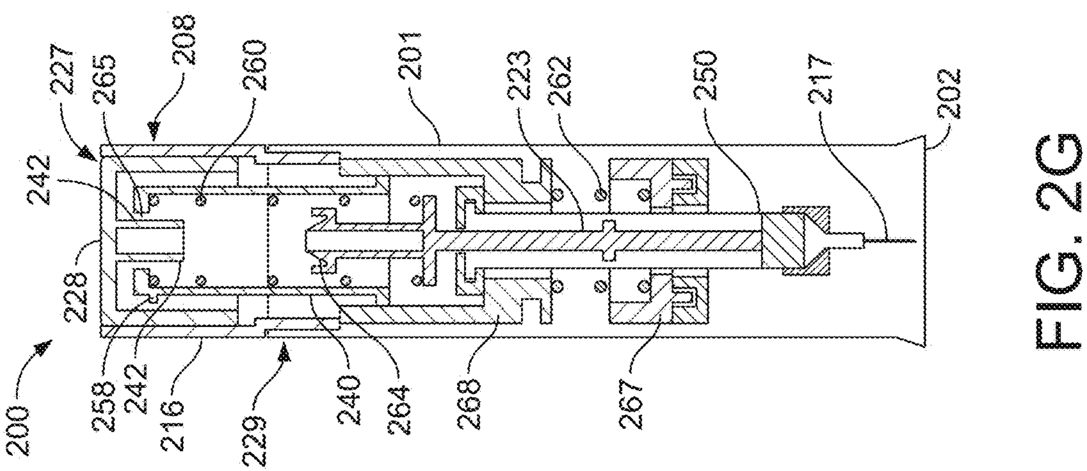
FIG. 2G
FIG. 2F
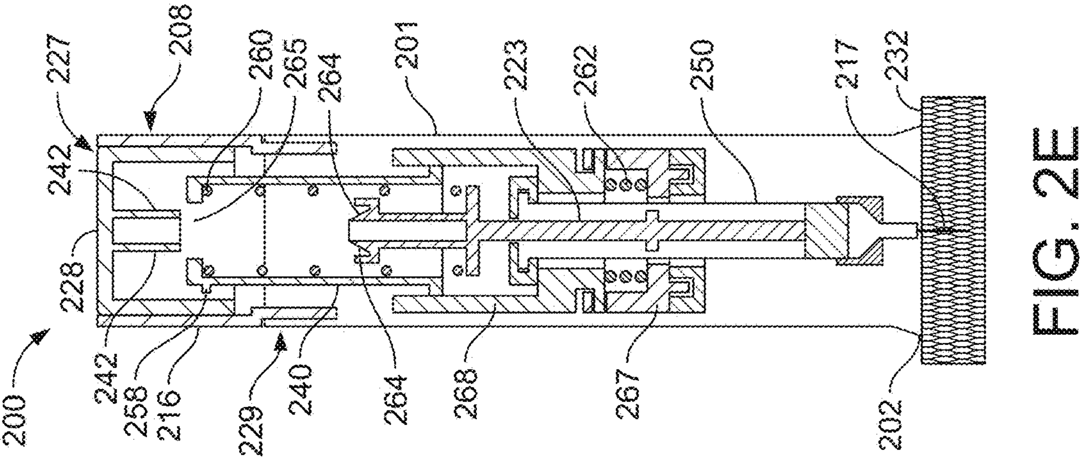
FIG. 2E 311
313
342
312
331
304
340
341

342
331
304
340
341

311
313
312

MEDICAMENT DELIVERY DEVICE

TECHNICAL FIELD

The present disclosure relates to a medicament delivery device, to methods of preparing a medicament delivery device for use prior to dispensing medicament from the medicament delivery device, and to methods of manufacturing or assembling a medicament delivery device.

BACKGROUND

Medicament delivery devices, such as auto-injectors, are known in the art for dispensing medicament to an injection site of a patient. In some cases, the needle actuator can be depressed accidentally, for example, before the device is ready and/or in position for use. Depressing the needle actuator accidentally can cause a dose of medicament to be unintentionally dispensed. This can lead to a waste of medicament.

SUMMARY

According to a first aspect of the disclosure, there is provided a medicament delivery device comprising a body comprising a proximal end and a distal end defining a longitudinal axis; a needle for injecting medicament; an actuation member moveable relative to the body along the longitudinal axis for actuating the medicament delivery device; a lock ring configured to rotate relative to the body about the longitudinal axis between a first position in which the actuation member is not permitted to move along the longitudinal axis relative to the body, and a second position in which the actuation member is permitted to move along the longitudinal axis relative to the body; and a cap arrangeable in a capped position in which the cap abuts with and conceals the distal end of the body to conceal the needle; wherein when the cap is in the capped position the lock ring is in a first state in which the lock ring is in the first position and is not permitted to rotate towards the second position; and wherein moving the cap in a distal direction away from the distal end of the body along the longitudinal axis away from the capped position causes the lock ring to be in a second state in which the lock ring is permitted to rotate from the first position towards the second position.

In some embodiments, the medicament delivery device comprises a proximal end and a distal end. In some embodiments, the proximal end of the body corresponds with the proximal end of the medicament delivery device, and the distal end of the body corresponds with the distal end of the medicament delivery device. In some embodiments, the proximal end of the body is arranged proximate to the proximal end of the medicament delivery device, and the distal end of the body is arranged proximate to the distal end of the medicament delivery device.

In some embodiments, the actuation member is arranged at the proximal end of the body and the needle is arranged at the distal end of the body.

In some embodiments, the distal direction is generally parallel to the longitudinal axis and is away from the proximal end of the body and towards the distal end of the body. In some embodiments, a proximal direction is opposite to the distal direction and is generally parallel to the longitudinal axis and is away from the distal end of the body and towards the proximal end of the body.

In some embodiments, the body and/or the lock ring are each generally cylindrical.

In some embodiments, the lock ring is arranged adjacent to the body along the longitudinal axis.

In some embodiments, at least a portion of the lock ring is arranged to overlap with at least a portion of the body along the longitudinal axis. In some embodiments, at least a portion of the lock ring is arranged to circumscribe at least a portion of the body about the longitudinal axis.

In some embodiments, the body is configured to house the needle.

In some embodiments, the needle is moveable between a retracted position in which the needle is arranged inside the body, and an extended position in which the needle is arranged to protrude from the distal end of the body. In some embodiments, when the needle is in the extended position, a distal end of the needle is arranged to protrude from the distal end of the body. In some embodiments, moving the needle relative to the body along the distal direction moves the needle from the retracted position to the extended position In some embodiments, when the lock ring is in the first position the actuation member is in a locked position, and when the lock ring is in the second position the actuation member is in an unlocked position.

In some embodiments, the cap is removably couplable to the body.

In some embodiments, the cap comprises a main body portion, and a needle shield portion which protrudes from the main body portion into the body of the medicament delivery device at the distal end of the body and which is configured to circumscribe and shield the needle when the cap is in the capped position. In some embodiments, the main body portion is generally cylindrical, and/or the needle shield portion is generally cylindrical and hollow.

In some embodiments, when the cap is in the capped position, a contact surface of the cap is arranged to be in contact with and/or abut a contact surface of the body at the distal end of the body. In some embodiments, when the cap is in an uncapped position or an intermediate position, the contact surface of the cap is arranged to be spaced apart from the contact surface of the body along the longitudinal axis. In some embodiments, moving the cap in the distal direction away from the distal end of the body along the longitudinal axis away from the capped position causes the contact surface of the cap to be moved apart from the contact surface of the body.

In some embodiments, the cap is arrangeable in an uncapped position in which the cap is decoupled from the body.

In some embodiments, the cap is arrangeable in an uncapped position in which the cap does not abut with and does not conceal the distal end of the body to conceal the needle. In some embodiments, when the cap is in the uncapped position, no portion of the cap is arranged inside the body.

In some embodiments, when the cap is in an intermediate position, at least a portion of the cap is arranged inside the body, and a contact surface of the cap is arranged to be spaced apart from a contact surface of the body at the distal end of the body.

In some embodiments, the medicament delivery device is arrangeable in a pre-use state in which the lock ring is in the first position and is in the first state, and the cap is in the capped position. In some embodiments, when the medicament delivery device is in the pre-use state, the needle is arranged in a retracted position inside the body.

In some embodiments, the medicament delivery device is arrangeable in a ready for use state in which the lock ring is in the second state and is permitted to be rotatable into the second position. In some embodiments, when the medicament delivery device is arranged in the ready for use state, the lock ring is in the second position, and the cap is not in the capped position.

In some embodiments, when the medicament delivery device is arranged in the ready for use state, the actuation member may be moved along the longitudinal axis in the distal direction to actuate the medicament delivery device, causing the needle to be moved from the retracted position into an extended position in which at least a portion of the needle protrudes from the distal end of the body.

In some embodiments, when the lock ring is in the first state the lock ring is not permitted to rotate about the longitudinal axis relative to the body, and when the lock ring is in the second state the lock ring is permitted to rotate about the longitudinal axis relative to the body.

In some embodiments, moving the cap in the distal direction away from the capped position causes the cap to be decoupled from the body.

In some embodiments, moving the cap in the distal direction away from the capped position causes the lock ring to be moveable relative to the body.

In some embodiments, moving the cap in the distal direction away from the capped position causes the lock ring to be rotatable relative to the body about the longitudinal axis.

In some embodiments, moving the cap in the distal direction away from the capped position allows the lock ring to be rotatable relative to the body about the longitudinal axis.

In some embodiments, moving the cap in the distal direction away from the capped position causes the lock ring to become rotatable relative to the body about the longitudinal axis.

In some embodiments, when the lock ring is in the second state in which the lock ring is permitted to rotate from the first position towards the second position, the lock ring is automatically caused to rotate from the first position towards the second position upon movement of the cap in the distal direction, or the lock ring is automatically caused to become rotatable such that a user of the medicament delivery device may manually rotate the lock ring from the first position towards the second position.

In some embodiments, moving the cap in the distal direction away from the capped position permits rotational movement of the lock ring relative to the body about the longitudinal axis, for example such that a user of the medicament delivery device may manually rotate the lock ring about the longitudinal axis to move it from the first position into the second position.

In some embodiments, moving the cap in the distal direction away from the capped position causes the lock ring to rotate about the longitudinal axis relative to the body, for example automatically, for example such that manual user rotation of the lock ring is not required.

In some embodiments, the actuation member is moveable relative to the body along the longitudinal axis in the distal direction from a first position, to a second position for dispensing medicament from the needle. In some embodiments, when the cap is in the capped position the actuation member is in the first position, and when the cap is in an uncapped position the actuation member is permitted to be moved into the second position. In some embodiments, the actuation member is arrangeable in one or more intermediate positions between the first position and the second position.

In some embodiments, the actuation member is arrangeable in an extended position, in which at least a portion of the actuation member is arranged to protrude from the lock ring at the proximal end of the medicament delivery device by a first amount; and a retracted position, in which the actuation member is arranged to protrude out from the lock ring at the proximal end of the medicament delivery device by a second amount that is less than the first amount.

In some embodiments, the actuation member is arrangeable in an extended position, in which at least a portion of the actuation member is arranged to protrude from the lock ring at the proximal end of the medicament delivery device by a first amount; and a retracted position, in which the actuation member is arranged inside the lock ring to be generally flush therewith at a proximal end of the lock ring, such that the actuation member does not protrude from the lock ring.

In some embodiments, moving the actuation member in the distal direction causes the actuation member to be moved from the extended position into the retracted position, to actuate the medicament delivery device. In some embodiments, when the cap is in the capped position the actuation member is in the extended position, and when the cap is in an uncapped position the actuation member is permitted to be moved into the retracted position. In some embodiments, the actuation member is arrangeable in one or more intermediate positions between the extended position and the retracted position.

In some embodiments, the actuation member comprises a button configured to be pressed by a user to move the actuation member along the distal direction. In some embodiments, the actuation member comprises a generally cylindrical button.

In some embodiments, the actuation member comprises a lever and/or a slidable element.

In some embodiments, the actuation member is slidable inside the body along the longitudinal axis relative to the body.

In some embodiments, movement of the actuation member in the distal direction relative to the body causes the needle to be moved from the retracted position to the extended position.

In some embodiments, at least a portion of the lock ring is arranged to circumscribe and receive at least a portion of the actuation member. In some embodiments, at least a portion of the actuation member is arranged concentrically inside the lock ring.

In some embodiments, the medicament delivery device further comprises a first biasing member configured to bias the actuation member towards the first position.

In some embodiments, the needle is moveable along the longitudinal axis relative to the body between: a retracted position in which the needle is arranged inside the body, and an extended position for delivering medicament in which at least a portion of the needle protrudes from the distal end of the body; wherein moving the actuation member from the first position to the second position along the distal direction causes the needle to be moved from the retracted position to the extended position.

In some embodiments, the medicament delivery device further comprises a blocking element configured to obstruct rotational movement of the lock ring about the longitudinal axis relative to the body; wherein the blocking element is arrangeable in a first position in which the lock ring is in the first state, and a second position in which the lock ring is in the second state; wherein moving the cap along the distal direction causes the blocking element to move from the first position to the second position.

In some embodiments, the blocking element is configured to engage with and/or interface with the lock ring to obstruct rotational movement of the lock ring about the longitudinal axis relative to the body, to provide for the first and second states of the lock ring.

In some embodiments, moving the blocking element from the first position to the second position comprises moving the blocking element along the longitudinal axis relative to the body in the distal direction.

In some embodiments, the blocking element comprises a radial protrusion arranged to extend generally normal to the longitudinal axis.

In some embodiments, the blocking element is integrally formed with or coupled to the body.

In some embodiments, the body is an outer body, and the blocking element is integrally formed with or coupled to an inner body arranged inside the outer body and moveable relative thereto along the longitudinal axis.

In some embodiments, the body is an outer body and the device further comprises an inner body comprising the blocking element and arranged inside the outer body and moveable relative thereto along the longitudinal axis; wherein the inner body is removably couplable to the cap such that when the cap is in the capped position the inner body is coupled to the cap such that movement of the cap in the distal direction causes the inner body to move relative to the outer body along the distal direction together with the cap.

In some embodiments, the inner body is hollow and generally cylindrical.

In some embodiments, the inner body is rotationally fixed relative to the outer body such that the inner body cannot rotate relative to the outer body about the longitudinal axis.

In some embodiments, the inner body comprises a spring guide and is configured to house one or more biasing members such as one or more springs.

In some embodiments, the inner body comprises a plurality of blocking elements. In some embodiments, the plurality of blocking elements are equally spaced apart from one another about the longitudinal axis.

In some embodiments, the inner body further comprises one or more stopper portions configured to engage with one or more respective stoppers arranged to protrude radially inwards towards the inner body from an inner surface of the outer body, to limit the axial range of motion of the inner body relative to the outer body along the longitudinal axis.

In some embodiments, the inner body further comprises one or more engagement portions for engaging with the cap, such that the inner body may be removably coupled to the cap.

In some embodiments, during movement of the cap in the distal direction along a first axial range of motion the inner body is coupled to the cap and the blocking element is caused to move from the first position into the second position; and completion of the movement of the cap along the first axial range of motion causes the cap to become decoupled from the inner body, such that the inner body is decoupled from the cap during movement of the cap in the distal direction along a subsequent second axial range of motion.

In some embodiments, the cap comprises one or more arms extending generally parallel to the longitudinal axis and each comprising a clip configured to form a snap fit with the inner body to couple the inner body to the cap; wherein completion of the movement of the cap along the first axial range of motion causes the one or more arms to deflect or flex relative to the inner body to decouple the cap from the inner body.

In some embodiments, each of the one or more arms of the cap is an axially extending arm.

In some embodiments, each of the one or more arms of the cap comprises a fixed end and a free end opposite the fixed end. In some embodiments, the clip is arranged at the free end. In some embodiments, the clip is generally triangular or wedge shaped. In some embodiments, each of the clips is configured to hook onto and/or around a respective one of the engagement portions of the inner body, in order to form a snap fit therewith to couple the cap to the inner body.

In some embodiments, when the cap is coupled to the inner body, movement of the cap along the longitudinal axis in the distal direction relative to the outer body causes the inner body to also move along the longitudinal axis in the distal direction relative to the outer body.

In some embodiments the cap comprises a pair of arms diametrically opposed to one another.

In some embodiments, the medicament delivery device further comprises one or more stoppers configured to limit the axial range of motion of the inner body relative to the outer body along the longitudinal axis.

In some embodiments, each of the one or more stoppers is configured to protrude radially inwards from an inner surface of the outer body.

In some embodiments, the blocking element comprises a radially protruding element configured to be received in a receiving segment of the lock ring when the blocking element is in the second position, to permit the lock ring to rotate relative to the blocking element about the longitudinal axis.

In some embodiments, the lock ring comprises a first annular portion and a second annular portion arranged along the longitudinal axis; wherein the first annular portion comprises a first receiving segment configured to receive the blocking element and which extends around a first portion of the circumference of the lock ring; wherein the second annular portion comprises a second receiving segment configured to receive the blocking element and which extends around a second portion of the circumference of the lock ring; wherein each of the first and second receiving segments comprises an aperture, recess, channel, groove or cut-out; and wherein the second portion is larger than the first portion, such that when the blocking element is received in the first receiving segment the blocking element is in the first position and when the blocking element is received in the second receiving segment the blocking element is in the second position.

In some embodiments, when the blocking element is received in the first receiving segment the lock ring is in the first state in which the lock ring is in the first position and is not permitted to rotate towards the second position, and when the blocking element is received in the second receiving segment the lock ring is in the second state in which it is permitted to rotate from the first position towards the second position.

In some embodiments, the second portion subtends around a larger angle or length of the circumference of the lock ring than the first portion.

In some embodiments, the first receiving segment does not extend around the entire circumference of the first annular portion along the circumferential direction.

In some embodiments, the first receiving segment does not extend around the entire circumference of the lock ring along the circumferential direction.

In some embodiments, the second receiving segment does not extend around the entire circumference of the second annular portion along the circumferential direction.

In some embodiments, the second receiving segment does not extend around the entire circumference of the lock ring along the circumferential direction.

In some embodiments, the second receiving segment extends around substantially the entire circumference of the second annular portion along the circumferential direction.

In some embodiments, the second receiving segment extends around substantially the entire circumference of the lock ring along the circumferential direction.

In some embodiments, the second receiving segment is larger than the first receiving segment along the circumferential direction.

In some embodiments, the second receiving segment is arranged to extend around a larger portion of the circumference of the lock ring than the first receiving segment.

In some embodiments, the range of rotational motion possible of the lock ring about the longitudinal axis relative to the outer body is larger when the blocking element is received in the second annular portion of the lock ring than when the blocking element is received in the first annular portion of the lock ring.

In some embodiments, along the circumferential direction, the first receiving segment is sized to be approximately the same size as the blocking element.

In some embodiments, along the circumferential direction, the second receiving segment is sized to be larger than the blocking element.

In some embodiments, the first annular portion is arranged adjacent to the second annular portion along the longitudinal axis.

In some embodiments, the first annular portion is spaced apart from the second annular portion along the longitudinal axis.

In some embodiments, the first annular portion is arranged closer to the proximal end of the medicament delivery device than the distal end of the medicament delivery device, and the second annular portion is arranged closer to the distal end of the medicament delivery device than the proximal end of the medicament delivery device.

In some embodiments, the first annular portion and the second annular portion each extends around a circumferential direction about the longitudinal axis, wherein the circumferential direction circumscribes the longitudinal axis.

In some embodiments, when the cap is in the capped position the blocking element is arranged in the first receiving segment.

In some embodiments, when the cap is in the capped position the blocking element is aligned with the first annular portion along the longitudinal direction.

In some embodiments, movement of the cap in the distal direction away from the capped position causes the blocking element to move from the first receiving segment into the second receiving segment.

In some embodiments, movement of the cap in the distal direction away from the capped position causes the blocking element to move from being aligned with the first annular portion to being aligned with the second annular portion along the longitudinal direction.

In some embodiments, the first annular portion comprises a first blocking segment and the second annular portion comprises a second blocking segment.

In some embodiments, the remainder of the first annular portion which does not comprise the first receiving segment comprises the first blocking segment; and the remainder of the second annular portion which does not comprise the second receiving segment comprises the second blocking segment. In some embodiments, the first receiving segment extends around a first portion of the circumference of the first annular portion, and the first blocking segment extends around the remainder of the circumference of the first annular portion. In some embodiments, the second receiving segment extends around a first portion of the circumference of the second annular portion, and the second blocking segment extends around the remainder of the circumference of the second annular portion.

In some embodiments, the first blocking segment and the second blocking segment are each generally solid.

In some embodiments, the first and second blocking segments are configured to engage with the blocking element.

In some embodiments, the first and second blocking segments are configured to obstruct the blocking element.

In some embodiments, movement of the blocking element along the longitudinal axis causes the lock ring to rotate about the longitudinal axis.

In some embodiments, the lock ring comprises an inclined surface that is angled relative to a circumferential direction of the lock ring which circumscribes the longitudinal axis, wherein the blocking element is configured to engage with the inclined surface, such that movement of the blocking element along the longitudinal axis causes the inclined surface to move relative to the blocking element to cause the lock ring to rotate about the longitudinal axis.

In some embodiments, between the proximal end and the distal end of the medicament delivery device, i.e. along the distal direction, the inclined surface is angled towards the distal end of the medicament delivery device.

In some embodiments, the inclined surface comprises a ramp.

In some embodiments, the inclined surface is generally straight and linear.

In some embodiments, at least a portion of the inclined surface is curved.

In some embodiments, the blocking element is configured to bear against the inclined surface.

In some embodiments, the inclined surface is configured to move relative to the blocking element. In some embodiments, the inclined surface is configured to rotate relative to the blocking element. In some embodiments, the inclined surface is configured to slide relative to the blocking element.

In some embodiments, the inclined surface is configured to convert axial movement of the blocking element along the distal direction to rotational movement of the lock ring about the longitudinal axis relative to the outer body.

In some embodiments, the lock ring comprises a receiving element comprising a slot, a groove, a channel, an aperture or a cut-out configured to receive the blocking element;

wherein the receiving element comprises a first portion extending generally parallel to the longitudinal axis, and a second portion extending generally along a circumferential direction which circumscribes the longitudinal axis and/or extending at an angle relative to said circumferential direction.

In some embodiments, the second portion comprises the inclined surface.

In some embodiments, the second portion is angled relative to the first portion. In some embodiments, the second portion is generally perpendicular to the first portion. In some embodiments, the receiving element is generally L-shaped.

In some embodiments, the first portion and/or the second portion are generally straight and linear.

In some embodiments, at least a portion of the first portion and/or the second portion is generally curved.

In some embodiments, the receiving element comprises one or more additional portions.

In some embodiments, when the cap is in the capped position the blocking element is configured to be received in the first portion of the receiving element of the lock ring.

In some embodiments, moving the cap in the distal direction away from the distal end of the body along the longitudinal axis away from the capped position causes relative movement between the blocking element and the first portion such that the blocking element is relatively moved towards the second portion of the receiving element of the lock ring.

In some embodiments, relative movement between the blocking element and the second portion causes the lock ring to rotate from the first position towards the second position.

In some embodiments, the first portion comprises a proximal end and a distal end, wherein the second portion is connected to the first portion at the distal end of the first portion.

In some embodiments, moving the cap along the distal direction causes the blocking element to move along the distal direction relative to and along the first portion of the receiving element, from the proximal end of the first portion to the distal end of the first portion.

In some embodiments, movement of the blocking element into the distal end of the first portion of the receiving element permits the lock ring to rotate about the longitudinal axis relative to the blocking element.

In some embodiments, moving the cap in the distal direction away from the capped position causes the lock ring to be rotatable from the first position towards the second position.

In some embodiments, moving the cap in the distal direction away from the capped position causes the lock ring to rotate from the first position towards the second position.

In some embodiments, the medicament delivery device further comprises: a plunger removably couplable to the inner body and configured to place the needle in an injection position for injecting medicament, wherein moving the actuation member relative to the outer body along the longitudinal axis to actuate the medicament delivery device causes the plunger to become decoupled from the inner body and to move along the distal direction; and a second biasing member, for example a spring, configured to bias the plunger towards the distal end of the body, wherein the second biasing member is arranged inside the inner body.

In some embodiments, the plunger comprises one or more deflectable arms each comprising a clip configured to be received in an aperture of the inner body to couple the plunger to the inner body; wherein moving the actuation member in the distal direction causes each of the one or more deflectable arms to deflect relative to the longitudinal axis to cause the clip to be moved out from the aperture to permit the plunger to move relative to the inner body along the distal direction.

In some embodiments, moving the actuation member in the distal direction causes each of the one or more deflectable arms to deflect relative to the longitudinal axis to cause the clip to be moved out from the aperture to decouple the plunger from the inner body to permit the plunger to move relative to the inner body along the distal direction.

In some embodiments, each of the one or more deflectable arms of the plunger comprises a fixed end and a free end opposite the fixed end. In some embodiments, the clip of each of the one or more deflectable arms is arranged at the free end. In some embodiments, the clip is generally triangular or wedge shaped. In some embodiments, the clip is configured to be received in the aperture of the inner body to form a snap fit therewith, to couple the plunger to the inner body.

In some embodiments, deflection of the one or more deflectable arms relative to the longitudinal axis causes the clip to be unhooked from the aperture of the inner body to decouple the snap fit.

In some embodiments, the one or more deflectable arms are caused to deflect and move along the distal direction by applying a force to the plunger along the distal direction by actuating the actuation member and moving it from the first position to the second position.

In some embodiments, the plunger is arranged inside the outer body.

In some embodiments, at least a portion of the plunger is arranged inside the inner body.

In some embodiments, the plunger is configured to be moved along the distal direction to move the needle from a retracted position into an extended position. In some embodiments, moving the plunger along the distal direction relative to the outer body causes the needle to be placed in the injection position for injecting medicament, in which the needle is arranged to protrude from the distal end of the body.

In some embodiments, the actuation member comprises a receiving portion for engagement with the plunger.

In some embodiments, the receiving portion is generally cylindrical and hollow and is arranged to protrude away from an actuation surface of the actuation member into the lock ring, and the receiving portion may be generally coincident with the longitudinal axis.

In some embodiments, the receiving portion is configured to fit over and/or around the clips of the one or more deflectable arms of the plunger, such that movement of the actuation member in the distal direction by pressing the actuation member, for example from an extended position into a retracted position, to actuate the medicament delivery device, causes the receiving portion to push down on the clips in the distal direction, and to circumscribe the clips. This may cause the clips to be pushed radially inwards towards the longitudinal axis. This may cause the one or more deflectable arms to be deflected or flexed inwards, to unhook the clips from the aperture of the inner body, thus causing the plunger to become decoupled from the inner body, to permit the plunger to be moved along the distal direction in order to move the needle into a position for injection.

In some embodiments, the medicament delivery device contains medicament.

According to a second aspect of the disclosure, there is provided a method of preparing a medicament delivery device according to the first aspect of the disclosure for use prior to dispensing medicament from the medicament delivery device. The method comprises: removing the cap from the outer body by moving it from the capped position along the distal direction; moving the lock ring from the first position to the second position by rotating the lock ring about the longitudinal axis relative to the outer body; and moving the actuation member along the longitudinal axis to actuate the medicament delivery device.

In some embodiments, the medicament delivery device comprises any one or more of the optional features described above in relation to the first aspect of the disclosure.

In some embodiments, the step of removing the cap from the outer body by moving it from the capped position along the distal direction permits the step of moving the lock ring from the first position to the second position by rotating the lock ring about the longitudinal axis relative to the outer body to occur.

In some embodiments, when the cap is in the capped position the lock ring is in the first state in which the lock ring is in the first position and is not permitted to rotate towards the second position; and moving the cap in the distal direction to decouple the cap from the outer body causes the lock ring to be in the second state in which the lock ring is permitted to rotate from the first position towards the second position.

In some embodiments, the step of moving the lock ring from the first position to the second position by rotating the lock ring about the longitudinal axis relative to the outer body is performed manually after the step of removing the cap from the outer body by moving it from the capped position along the distal direction.

In some embodiments, the step of moving the lock ring from the first position to the second position by rotating the lock ring about the longitudinal axis relative to the outer body occurs automatically as a result of the performance of the step of removing the cap from the outer body by moving it from the capped position along the distal direction.

In some embodiments, the step of moving the lock ring from the first position to the second position by rotating the lock ring about the longitudinal axis relative to the outer body occurs subsequently after the step of removing the cap from the outer body by moving it from the capped position along the distal direction.

In some embodiments, the step of moving the lock ring from the first position to the second position by rotating the lock ring about the longitudinal axis relative to the outer body occurs at least partially simultaneously with the step of removing the cap from the outer body by moving it from the capped position along the distal direction.

In some embodiments, the step of moving the actuation member along the longitudinal axis to actuate the medicament delivery device comprises moving the actuation member in the distal direction from an extended position into a retracted position.

In some embodiments, the extended position is a presented position and the retracted position is a depressed position, wherein the actuation member comprises a button.

According to a third aspect of the disclosure, there is provided a method of preparing a medicament delivery device as claimed in claim 1 for use prior to dispensing medicament from the medicament delivery device, the method comprising: removing the cap from the body by moving it from the capped position along the distal direction; and then moving the actuation member along the longitudinal axis to actuate the device.

In some embodiments, the medicament delivery device comprises any one or more of the optional features described above in relation to the first aspect of the disclosure.

In some embodiments, the method comprises any one or more of the optional features or steps described above in relation to the second aspect of the disclosure.

According to a fourth aspect of the disclosure, there is provided a method of manufacturing or assembling a medicament delivery device, wherein the medicament delivery device is defined in claim 1. Further optional features of the medicament delivery device are described and/or contemplated here.

In some embodiments, the medicament delivery device comprises any one or more of the optional features described above in relation to the first aspect of the disclosure.

According to fifth aspect of the disclosure, there is provided a method of manufacturing or assembling a medicament delivery device, wherein the medicament delivery device has the features of any of the medicament delivery devices described and/or contemplated herein.

In some embodiments, the medicament delivery device comprises any one or more of the optional features described above in relation to the first aspect of the disclosure.

BRIEF DESCRIPTION OF THE DRAWINGS

Embodiments will now be described, by way of example only, with reference to the accompanying drawings, in which:

FIG. 2E is a schematic view of the device of FIG. 2A with the button having been pressed to release the dispensing mechanism;

FIG. 2F is a schematic view of the device of FIG. 2A showing the needle having retracted within the device after a dose has been delivered;

FIG. 2G is a schematic view of the device of FIG. 2A showing the device removed from the injection site after the needle has retracted within the device after delivery of the medicament;

DETAILED DESCRIPTION

Figures 1A, 1B:
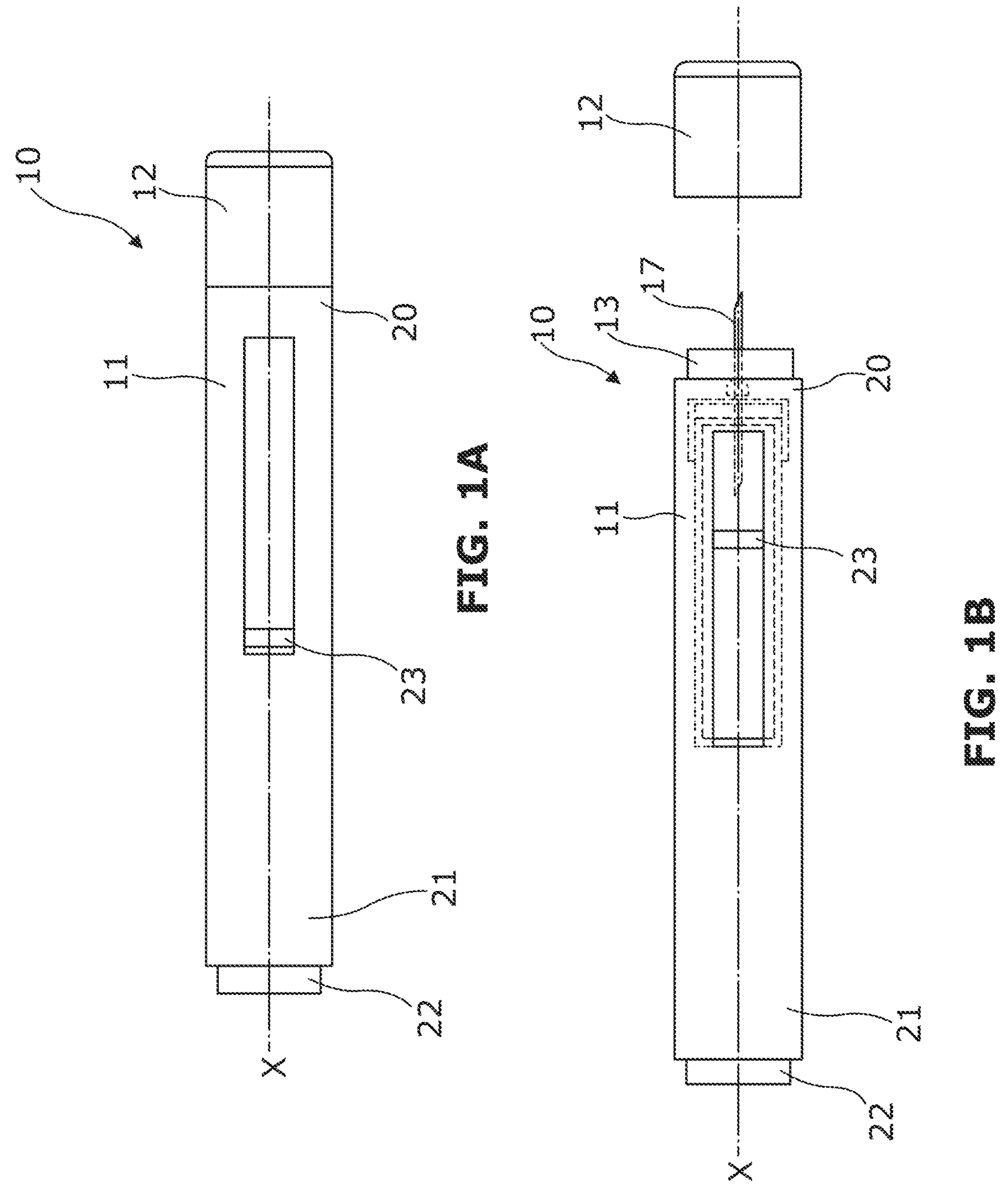
FIG. 1A shows a schematic view of a medicament delivery device with a cap attached.
FIG. 1B shows a schematic view of the medicament delivery device of FIG. 1A with the cap removed.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The dispensing mechanism provides one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The medicament delivery device can include various types of safety syringe, pen-injector, or auto-injector. The device can include a cartridge-based system that requires piercing a sealed ampule before use.

Distal movement of the actuation member may cause automatic dispensing of the medicament from the device and/or distal movement of the actuation member may cause the distal movement of the needle from a needle pre-use position to a needle injection position. The dispensing mechanism may be configured to dispense medicament from the needle when the dispensing mechanism is released.

In the needle pre-use position the needle may be flush with the distal end of the body or the needle may be recessed within the body. In another embodiment the needle may be fixed in position relative to the body.

In another device, different features may be provided to prevent the actuation member from moving distally. For example, the stop may be provided on another component of the medicament delivery device. In another device, a lock ring 216 is not present.

According to some embodiments of the present disclosure, an exemplary drug delivery device is shown in FIGS. 1A & 1B. The device 10, as described above, is configured to inject a medicament into a patient's body. The device 10 includes a housing 11 which typically contains a reservoir containing the medicament to be injected (e.g., a syringe) and the components required to facilitate one or more steps of the delivery process. The device 10 can also include a cap assembly 12 that can be detachably mounted to the housing 11. A user 10 typically removes the cap 12 from the housing 11 before the device 10 can be operated. As shown, the housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site. Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from the distal region 20 of the housing 11. Insertion of the needle 17 can occur via several mechanisms. For example, the needle 17 may be fixedly located relative to the housing 11 and initially be located within an extended needle sleeve 13. Proximal movement of the sleeve 13 by placing a distal end of the sleeve 13 against a patient's body and moving housing 11 in a distal direction will uncover the distal end of the needle 17.

Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of the sleeve 13 or by another form of activation, for example, a button 22. As shown in FIGS. 1A & 1B, the button 22 is located at a proximal end of the housing 11. However, in other embodiments, the button 22 could be located on a side of the housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through the needle 17. In some embodiments, a drive spring (not shown) is under compression before device 10 is activated. A proximal end of the drive spring can be fixed within the proximal region 21 of the housing 11, and a distal end of the drive spring can be configured to apply a compressive force to a proximal surface of the piston 23. Following activation, at least part of the energy stored in the drive spring can be applied to the proximal surface of the piston 23. This compressive force can act on the piston 23 to move it in a distal direction. Such distal movement acts to compress the liquid medicament within the syringe, forcing it out of the needle 17. Following injection, the needle 17 can be retracted within sleeve 13 or the housing 11. Retraction can occur when the sleeve 13 moves distally as a user removes device 10 from a patient's body. This can occur as the needle 17 remains fixedly located relative to the housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the device 10 can be locked as required.

FIGS. 2A to 2G show the sequential steps of operating a medicament delivery device 200. The medicament delivery device 200 is an autoinjector.

The device 200 comprises a body 201, a syringe 250 having a needle 217 and an axially moveable plunger 223 for dispensing medicament from the syringe 250. The device comprises a cap 254 which is removably attached to the body 201 and covers a distal end 202 of the body 201 for preventing access to the needle 217. The device has a needle shield 266 that covers the needle 217 before use. The needle shield 266 is attached to the cap 254.

The medicament delivery device 200 has a dispensing mechanism 229. The medicament delivery device 200 has an actuation member 227 which is configured to release the dispensing mechanism 229. The actuation member 227 is configured to engage the dispensing mechanism 229 to release the dispensing mechanism 229.

The dispensing mechanism 229 is configured to cause the needle 217 to move distally from a needle pre-use position, in which the needle 217 is recessed within the body 201, to an injection position in which the needle 217 protrudes from the distal end 202 of the body 201 when the dispensing mechanism 229 is released.

The dispensing mechanism 229 is configured to dispense the medicament from the needle 217 when the needle 217 is in the injection position.

Figures 2A, 2B, 2C, 2D:
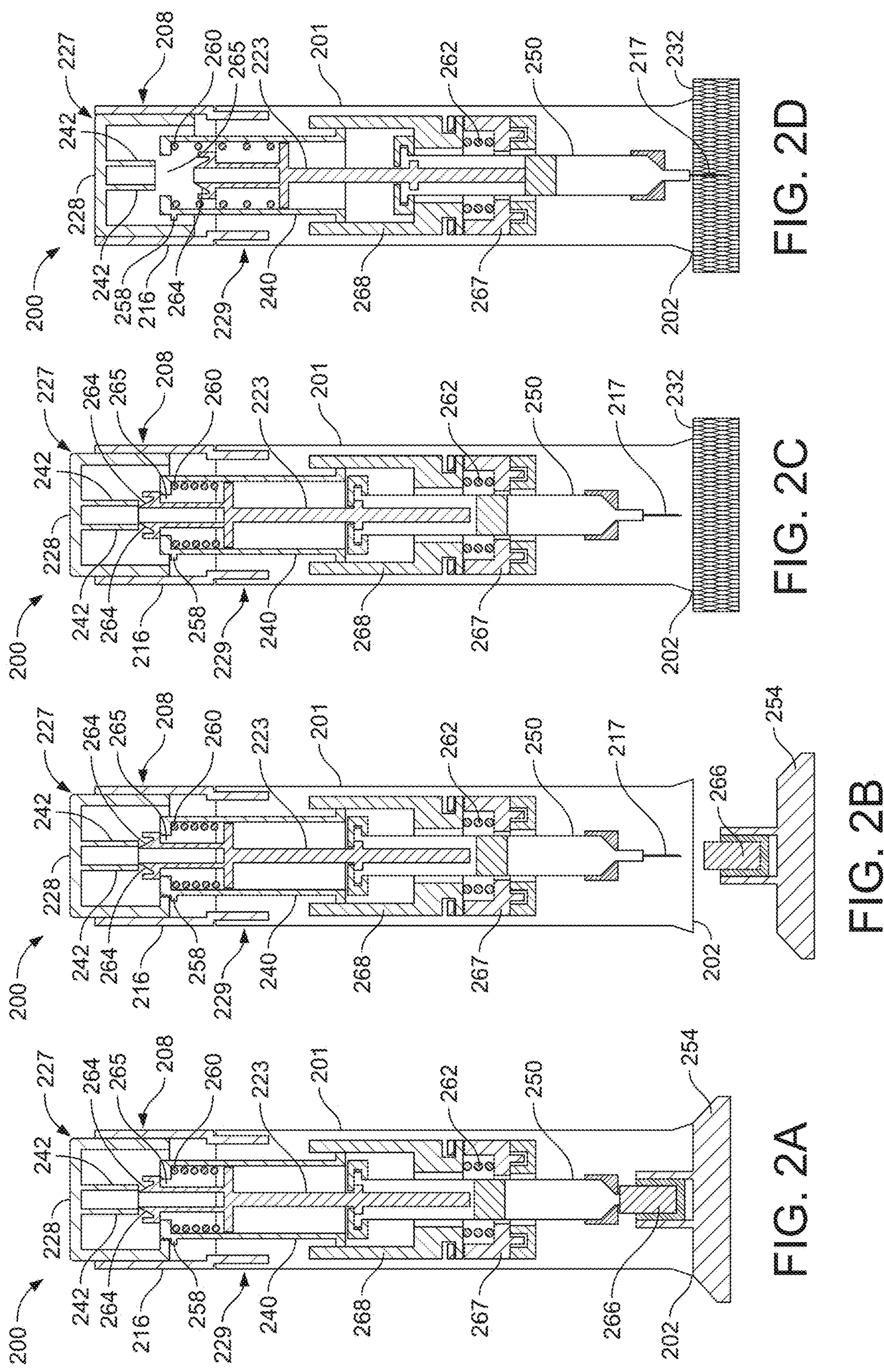
FIG. 2A is a schematic view of a medicament delivery device prior to use (i.e. in a pre-use configuration)
FIG. 2B is a schematic view of the device of FIG. 2A with the cap removed.
FIG. 2C is a schematic view of the device of FIG. 2A showing the device placed at an injection site.
FIG. 2D is a schematic view of the device of FIG. 2A with the button having been pressed to release the dispensing mechanism.

As shown in FIGS. 2B-2C, in order to deliver a dose of medicament to an injection site, the cap 254 is removed (FIG. 2B) and the device is placed at an injection site 232 (FIG. 2C).

The actuation member 227 comprises a button 228 and is prevented from being depressed by a stop 258. The stop is provided on the spring guide 240, for example.

The device has a locking member 208 in the form of a lock ring 216 which is rotatable by a user about a longitudinal axis of the device. The actuation member 227 is keyed to the lock ring 216 so that the actuation member 227 rotates with the lock ring 216. The lock ring 216 is rotatable from a pre-use position, in which distal movement of the button 228 is prevented, to a use position in which distal movement of the button 228 is permitted.

When the lock ring 216 is in the pre-use position then the stop 258 engages the button 228 to prevent the button 228 from being depressed.

In order to allow the button 228 to be depressed, the lock ring 216 is rotated about the longitudinal axis of the device from the pre-use position to the use position. The rotation of the lock ring 216 also rotates the actuation member 227 to a position in which the stop 258 no longer prevents the button 228 from being depressed as shown, for example, in FIG. 2C.

Turning now to FIG. 2D, the user then presses the button 228 to release the dispensing mechanism 229 for dispensing medicament from the device. The dispensing mechanism 229 has a plunger 223 and a bias in the form of a compression spring 260. The plunger 223 is biased distally by the spring 260.

The dispensing mechanism 229 is at least partially housed within the spring guide 240. The plunger 223 has a release member which has proximally-extending clips 264. The spring 260 is retained in the compressed position by virtue of the clips 264 which protrude through a proximal opening 265 in the spring guide 240. The clips 264 engage the spring guide 240 for maintaining the plunger 223 in a proximal position.

The actuation member 227 has a firing member comprising a pair of protrusions 242 which engage with the clips 264 when the button 228 is depressed to flex the clips 264 radially inwardly thereby allowing the clips 264 to move distally through the proximal opening 265 to release the spring 260.

When the dispensing mechanism 229 is released, then the syringe 250 is released for distal axial movement towards the injection site 232 such that the needle 217 moves from the needle pre-use retracted position to an exposed (or "uncovered" or "injection") position for delivering medicament to the injection site 232 under the biasing force of the compression spring 260.

Depressing the button 228 releases the plunger 223 which, biased by the bias 260, moves along the syringe 250 towards the distal end of the device 200 to force medicament within the syringe 250 through the needle 217, thereby delivering a dose of medicament as shown, for example in FIG. 2E.

As shown in FIG. 2F, once the dose of medicament has been delivered, a medicament container bias 262, embodied by a further spring 262, then causes the needle 217 to move axially back to the retracted position, away from the injection site 232 in a proximal direction. The plunger 223 flexes a clip (not shown) on a first collar 267 which allows the first collar 267 to rotate relative to the body 201 and relative to a second collar 268. The first collar 267 rotates from a first position in which the second collar 268 is axially coupled to the first collar 267, into a second position in which the second collar 268 is free to move axially relative to the first collar 267. For example, the second collar 268 may comprise a radially protruding coupling element configured to be received in or engage with a corresponding receiving portion of the first collar 267, such that rotating the first collar 267 from the first position into the second position causes the coupling element to be moved out from the receiving portion, to allow the second collar 268 to move axially relative to the first collar 267. Axial movement of the second collar 268 permits the needle 217 to be retracted.

As shown in FIG. 2G, the device 200 is then removed from the injection site 232, for disposal.

The medicament delivery devices described herein may have some or all of the features as described in relation to the medicament delivery device 200.

The dispensing mechanism 229 may have the some or all of the features as described and/or contemplated in relation to FIGS. 2A to 2G.

In another embodiment, the dispensing mechanism may have alternative or additional features to those described and/or contemplated in relation to FIGS. 2A to 2G. The dispensing mechanism may have features as described and/or contemplated herein, for example in relation to FIGS. 1A and 1B.

FIGS. 3A to 3E show a medicament delivery device 300, which may be generally similar to the medicament delivery devices 10 and 200 shown in FIGS. 1A through to 2G and described above. The medicament delivery device 300 comprises an outer body 301, a needle 302, an actuation member 303, a lock ring 304 and a cap 305, which may be generally similar to and/or may be considered to be akin to the body 201, the needle 217, the actuation member 227, the lock ring 216, and the cap 254 respectively shown in FIGS. 2A to 2G and described above. The needle 302 is for injecting medicament from the medicament delivery device 300 and the actuation member 303 is for actuating the medicament delivery device 300. The lock ring 304 serves to provided locked and unlocked states of the actuation member 303 such that the medicament delivery device 300 may only be actuated and used when the actuation member 303 is in an unlocked state, as described below. The cap 305 is configured to be removably coupled to the body 302 in order to cover and conceal the needle 302, for reasons of hygiene and safety.

Figure 3A:
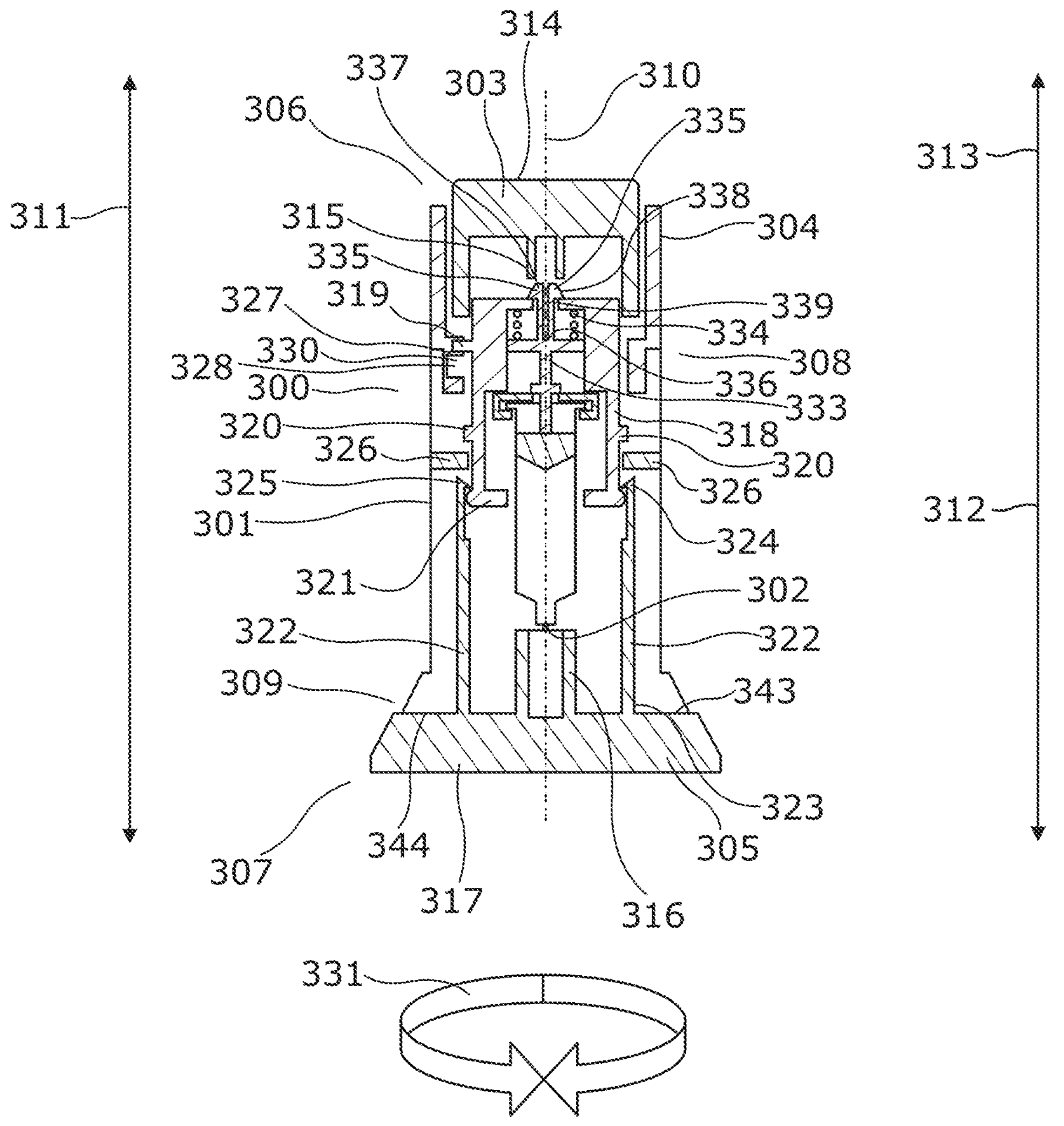
FIG. 3A shows a cross-sectional schematic view of a medicament delivery device with the cap in a capped position.

The medicament delivery device 300 comprises a proximal end 306 and a distal end 307, and the outer body 301 comprises a proximal end 308 and a distal end 309 which correspond with the proximal and distal ends 306, 307 respectively. That is, the proximal end 308 of the outer body 301 is arranged proximate to the proximal end 306 of the medicament delivery device 300, and similarly the distal end 309 of the outer body 301 is arranged proximate to the distal end 307 of the medicament delivery device 300. The proximal and distal ends 308, 309 of the outer body define a longitudinal axis 310. A longitudinal direction 311 of the medicament delivery device 300 is generally parallel to the longitudinal axis 310, as shown in FIG. 3A for example. Generally parallel to the longitudinal axis 310 and along the longitudinal direction 311, there is a distal direction 312 and a proximal direction 313 that is opposite to the distal direction 312. The distal direction 312 is defined as being away from the proximal ends 306, 308 and towards the distal ends 307, 309. Conversely, the proximal direction 313 is defined as being away from the distal ends 307, 309 and towards the proximal ends 306, 308.

In the example shown, the outer body 301 is hollow and is generally cylindrical, although it is also envisaged that the outer body 301 may have any other suitable shape or form. The lock ring 304 is also hollow and generally cylindrical in the example shown, although it is envisaged that the lock ring 304 may have any other suitable shape or form. For example, the outer body 301 and/or the lock ring 304 may have any suitable prismatic shape, such as a cuboid, triangular prism, pentagonal prism, hexagonal prism or octagonal prismatic shape. The lock ring 304 is arranged along the longitudinal direction 311 adjacent to the outer body 301 in the example shown, although it is also envisaged that at least a portion of the lock ring 304 and the outer body 301 may be arranged to overlap along the longitudinal direction 311, and/or that the lock ring 304 may for example be arranged to circumscribe at least a portion of the outer body 301 at the proximal end 308 thereof. The outer body 301 is arranged to house the needle 302 and the needle 302 is moveable relative to the outer body 301 along the longitudinal axis 310 between a retracted position (see FIG. 3D for example) and an extended position (see FIG. 3E for example). When the needle 302 is in the retracted position, the needle 302 is arranged inside the outer body 301, and when the needle 302 is in the extended position, the needle 302 is arranged to protrude from the distal end 309 of the outer body 301. The retracted position may be referred to as a proximal position and the extended position may be referred to as a distal position. The retracted or proximal position may be referred to as the needle 302 being in a pre-use state, and the extended or distal position may be referred to as the needle 302 being in a ready for use state. That is, when the needle 302 is in the extended or distal position, the needle 302 is ready to dispense medicament. The needle 302 may be moved relative to the outer body 301 along the distal direction 312 in order to move the needle from the retracted position/proximal position/pre-use state into the extended position/distal position/ready for use state.

In the example shown, the actuation member 303 comprises a generally cylindrical button, although it is also envisaged that the actuation member 303 may have any other suitable shape or form. For example, the actuation member 303 may comprise a lever or slideable element. The actuation member 303 is depressible, i.e. it can be pressed, by a user applying an actuation force in the distal direction 312 to an actuation surface 314 of the actuation member 303. When an actuation force is applied to the actuation surface 314 in the distal direction 312, the actuation member 303 is configured to move relative to the outer body 301 along the longitudinal axis 310, in the distal direction 312, in order to actuate the medicament delivery device 300. That is, the actuation member 303 is slidable inside the outer body 301 relative thereto along the longitudinal axis 310. Movement of the actuation member 303 in the distal direction 312 relative to the outer body 201 causes the needle 302 to be moved from the retracted position into the extended position, such that the medicament delivery device 300 may thus be placed in a state ready for use, so that medicament can be delivered from the needle 302, for example to a patient. Mechanisms for moving the needle 302 are known in the art and another embodiment may use a different mechanism for moving the needle 302 from the pre-use position to the use position. Mechanisms for dispensing the medicament from the needle 302 are known in the art and another embodiment may use a different mechanism. It may be desired to prevent the actuation member 303 from being pressed, i.e. to prevent the actuation member 303 from being actuatable, so that the medicament delivery device 300 cannot be actuated when the time is not right. For example, during transportation, storage or pre-use handling of the medicament delivery device 300, or when the cap 305 is still in the capped position concealing the needle 302, it may be desirable to prevent the actuation member 303 from being pressed, to avoid medicament being wasted and/or to avoid bending the needle 302—i.e. to prevent the medicament delivery device 300 from being actuated too soon. The lock ring 304 serves to selectively lock the actuation member 303 in place such that when the actuation member 303 is locked in place it is prevented from being moved along the longitudinal axis 310 relative to the outer body 301, such that the medicament delivery device 300 cannot be prematurely actuated. When the correct time is ready for the medicament delivery device 300 to be actuated, the lock ring 304 may then be moved to unlock the actuation member 303, such that the actuation member 303 is no longer prevented from being moved along the longitudinal axis 310 relative to the outer body 301, such that the medicament delivery device 300 may be actuated, as described below in more detail.

In the example shown, the lock ring 304 is arranged to circumscribe and radially receive a portion of the actuation member 303, such that a portion of the actuation member 303 is arranged concentrically inside the lock ring 304. The actuation member 303 is arrangeable in an extended position, which may also be referred to as a presented position, and a retracted position, which may also be referred to as a depressed position. When the actuation member 303 is arranged in the extended position, the actuation member 303 is arranged to protrude out from the lock ring 304 at the proximal end 306 of the medicament delivery device 300 by a first amount. When the actuation member 303 is arranged in the retracted position, the actuation member 303 is arranged to protrude out from the lock ring 304 at the proximal end 306 of the medicament delivery device 300 by a second amount that is less than the first amount, or the actuation surface 314 is arranged to be generally flush with a proximal end of the lock ring 304, such that the actuation member 303 does not protrude from the lock ring 304. Moving the actuation member 303 in the distal direction 312 causes the actuation member 303 to be moved from the extended position into the retracted position, to actuate the medicament delivery device.

In the example shown, the lock ring 304 is hollow and generally cylindrical, although other shapes and forms of lock ring 304 are also envisaged, for example prismatic shapes as aforementioned. The lock ring 304 is configured to rotate relative to the outer body 301 about the longitudinal axis 310 between a first position in which the actuation member 303 is not permitted to move along the longitudinal axis 310 in the distal direction 312 relative to the outer body 301, and a second position in which the actuation member 303 is permitted to move along the longitudinal axis 310 in the distal direction 312 relative to the outer body 301. In the example shown, when the lock ring 304 is in the first position, the actuation member 303 is in the extended position and is prevented from being moved into the retracted position; and when the lock ring 304 is in the second position, the actuation member 303 is permitted to move from the extended position into the retracted position. However, it is also envisaged that other longitudinal positions of the actuation member 303 relative to the outer body 301 along the longitudinal axis 310 are also possible, for example one or more intermediate positions between the extended and retracted positions, and also that the actuation member 303 need not necessarily initially be in the extended position when the lock ring 304 is in the first position. Therefore, it is to be understood that the actuation member 303 may be described generally as being moveable between a first position and a second position relative to the outer body 301 along the longitudinal axis 310, wherein movement of the actuation member 303 from the first position to the second position causes the medicament delivery device 300 to be actuated and/or for the needle 302 to be placed into an extended, ready to use position or injection state. Thus, it is to be understood that generally, when the lock ring 304 is in the first position, the actuation member 303 is prevented from moving from the first position into the second position, and when the lock ring 304 is in the second position the actuation member 303 is allowed to move from the first position into the second position. The medicament delivery device 300 may be configured such that rotating the lock ring 304 in an anticlockwise direction and/or in a clockwise direction about the longitudinal axis 310 relative to the outer body 301 causes the lock ring 304 to be moved from the first position towards or into the second position. When the lock ring 304 is in the first position, the actuation member 303 may be described as being in a locked state, and when the lock ring 304 is in the second position, the actuation member 303 may be described as being in a locked state.

The cap 305 serves to cover the distal end 309 of the outer body 301 and conceal the needle 302 before use of the medicament delivery device 300, i.e. before the user is ready to deliver medicament therefrom. In the example shown, the cap 305 comprises a generally cylindrical main body portion 317, and a hollow and generally cylindrical needle shield portion 316 which protrudes from the main body portion 317 into the outer body 301 at the distal end 309 thereof, to circumscribe and shield the needle 302. Although, it is envisaged that the cap 305 may have any other suitable shape or form. For example, the main body portion 317 need not necessarily be round or generally cylindrical but may be generally triangular, quadrilateral, pentagonal, hexagonal or octagonal for example, and the needle shield portion 316 need not necessarily be generally cylindrical but may have any other suitable prismatic shape for example.

Figures 3B, 3C:
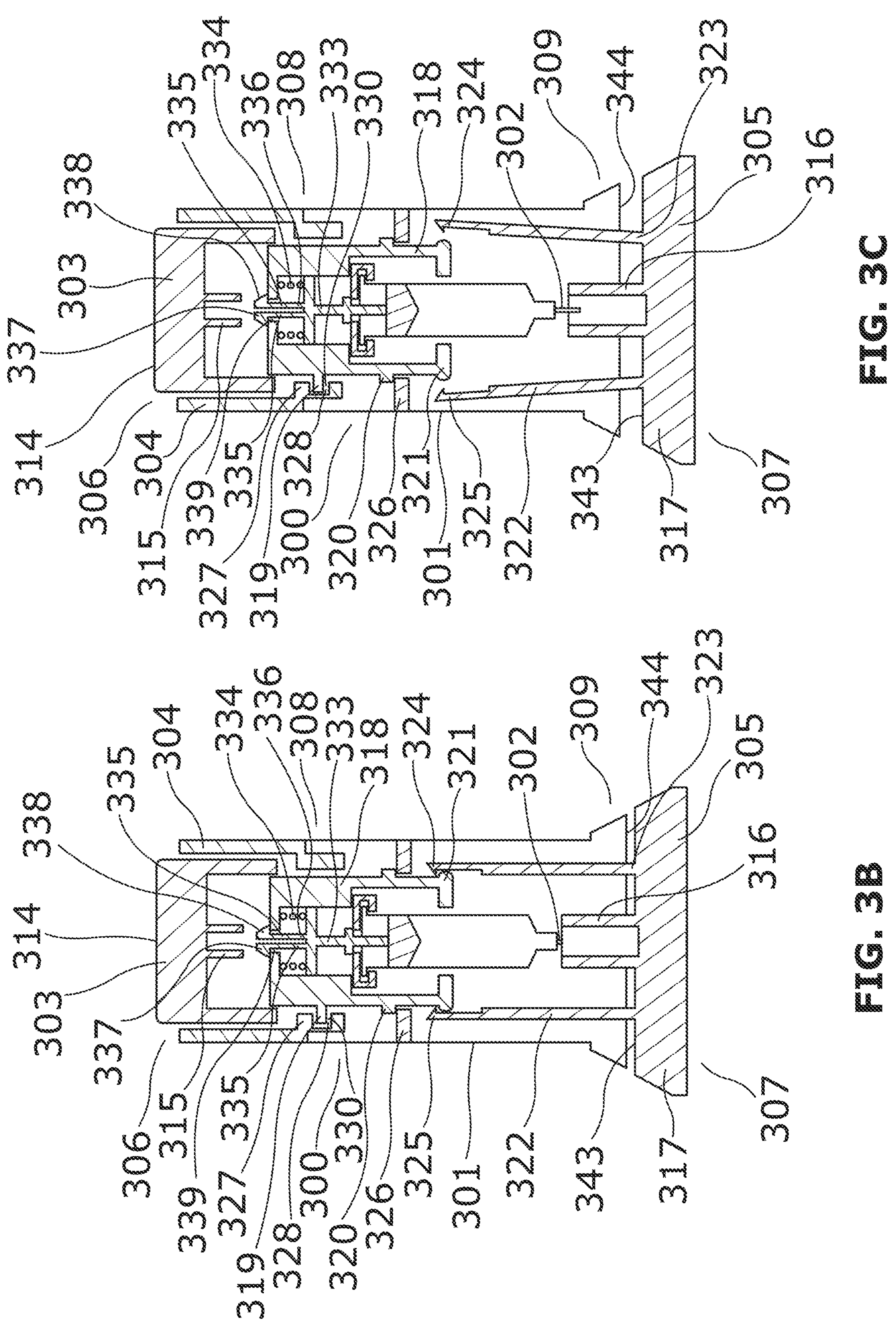
FIG. 3B shows a cross-sectional schematic view of a medicament delivery device with the cap in an intermediate position.
FIG. 3C shows a cross-sectional schematic view of a medicament delivery device with the cap in an intermediate position.
Figures 3D, 3E:
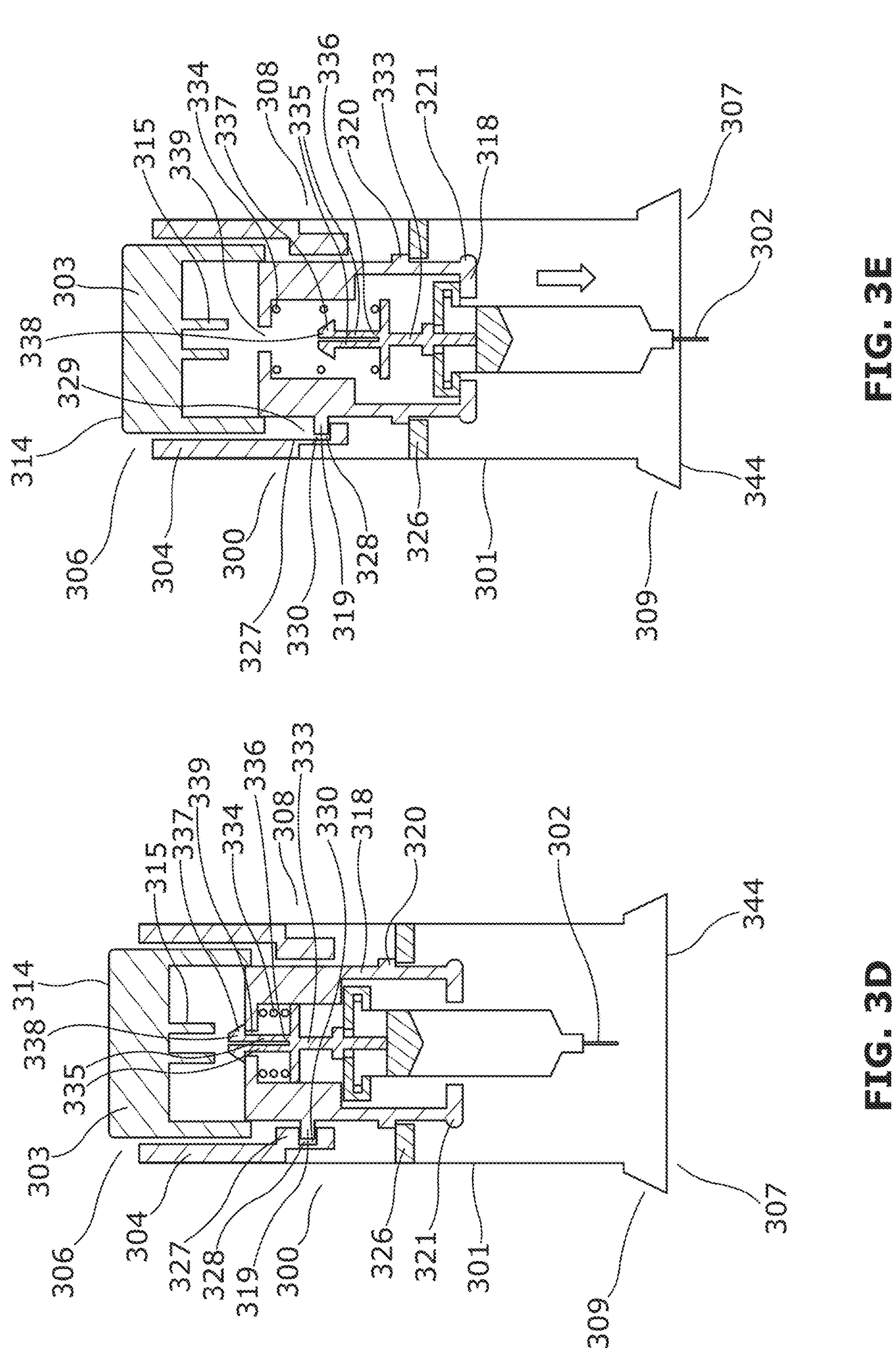
FIG. 3D shows a cross-sectional schematic view of a medicament delivery device with the cap removed.
FIG. 3E shows a cross-sectional schematic view of a medicament delivery device with the cap removed and in a ready for use state.

The cap 305 is removably couplable to the outer body 301 and is arrangeable in a capped position in which the cap 305 abuts with and conceals the distal end 309 of the outer body 301, to conceal the needle 302. When the cap 305 is in the capped position, for example as shown in FIG. 3A, a contact surface 343 of the cap 305 is arranged to be in contact with or otherwise abut a contact surface 344 of the outer body 301. In order to remove the cap 305 from the capped position, i.e. in order to decouple the cap 305 from the outer body 301 to expose the distal end 309 and the needle 302, the cap 305 may be moved away from the distal end 309 of the outer body 301 along the longitudinal axis 310 in the distal direction 312. This is sequentially shown in FIGS. 3A to 3C for example. As the cap 305 is moved out from the capped position along the distal direction 312, the contact surface 343 of the cap 305 is moved away from the contact surface 344 of the outer body 301, such that the contact surface 343 is arranged to be spaced apart from the contact surface 344 along the longitudinal axis 310, as shown in FIG. 3B for example. As the cap 305 is moved further along the distal direction 312, eventually, a portion of the cap 305 which is configured to protrude into and be arranged inside the outer body 301, for example one or more axially extending arms 322 which shall be described below in more detail, will eventually be moved so far along the distal direction 312 that it is/they are no longer arranged inside the outer body 301, and the cap 305 will then be completely decoupled from the outer body 301 and will no longer be in the capped position. In such a position, the cap 305 may be described as being in an uncapped position, which may also be referred to as an uncoupled position or a removed position. For example, FIGS. 3D and 3E show the cap 305 decoupled from the outer body 301 and hence removed from the remainder of the medicament delivery device 300. Relative to the longitudinal axis 310, when the cap 305 is between the capped position (see FIG. 3A for example) and the uncapped position (see FIGS. 3D and 3E for example), the cap 305 may be described as being in an intermediate position. FIGS. 3B and 3C show exemplary intermediate positions. When the cap 305 is in an intermediate position, the contact surface 343 is spaced apart from the contact surface 344, but a portion of the cap, for example one or more axially extended arms 322, may still at least partially be arranged inside the outer body 301. When the cap 305 is in an intermediate position, the cap 305 may be described as being in an uncoupled position.

The medicament delivery device 300 is configured such that when the cap 305 is in the capped position, i.e. wherein the contact surface 343 abuts and is in contact with the contact surface 344, the lock ring 304 is in a first state in which the lock ring 304 is in the aforementioned first position and is not permitted to rotate relative to the outer body 301 about the longitudinal axis 310, such that the lock ring 304 is not permitted to rotate towards the aforementioned second position. That is, when the cap 305 is in the capped position, the lock ring 304 is in the first position in which the actuation member 303 is in a locked state and is not permitted to move along the longitudinal axis 310 relative to the outer body 301, and the lock ring 304 is obstructed, blocked or otherwise prevented from being moved into the second position, so that the actuation member 303 cannot be moved from the locked state into the unlocked state. Thus, when the cap 305 is in place in the capped position, the actuation member 303 cannot be unlocked, so the medicament delivery device 300 cannot be actuated. Accordingly, the medicament delivery device 300 is advantageously prevented from being prematurely, accidentally and/or inadvertently actuated whilst the cap 305 is still in the capped position, which may advantageously avoid wasting medicament and/or avoid bending of the needle 302.

As shall be described below in more detail, the medicament delivery device 300 is configured such that moving the cap 305 away from the distal end 309 of the outer body 301 to decouple the cap 305 from the outer body 301 causes the lock ring 304 to be in a second state in which the lock ring 304 is permitted to rotate relative to the outer body 301 about the longitudinal axis 310, such that the lock ring 304 is permitted to rotate towards the aforementioned second position. Thus, moving the cap 305 out from the capped position, along the distal direction 312, for example into an intermediate position as seen in FIG. 3B or FIG. 3C for example, such that the contact surface 343 no longer contacts or abuts the contact surface 344, causes the lock ring 304 to become unlocked such that it is in a second state in which it may be rotated from the first position towards or into the second position. Accordingly, when the cap 305 is moved away from the capped position along the distal direction 312, the actuation member 303 may be permitted to move along the longitudinal axis 310 relative to the body 301, such that the medicament delivery device 300 may be actuated. As shall be described below in relation to the examples shown in FIGS. 3A through to 7B, it is envisaged that moving the cap 305 in the distal direction 312 away from the capped position to decouple the cap 305 from the outer body 301 permits the lock ring 304 to be movable from the first position in which the actuation member 303 is locked into or towards the second position in which the actuation member 303 is unlocked, either by permitting rotational movement of the lock ring 304 relative to the outer body 301 such that a user of the medicament delivery device 300 may manually rotate the lock ring 304 about the longitudinal axis 310 to move it into the second position, or by automatically causing the lock ring 304 to rotate relative to the outer body 301 into the second position, such that manual user rotation is not required.

The medicament delivery device 300 further comprises an inner body 318 arranged inside the outer body 301 and moveable relative thereto along the longitudinal axis 310. In the example shown, the inner body 318 is rotationally fixed relative to the outer body 301 such that the inner body 318 cannot rotate relative to the outer body 301 about the longitudinal axis 310. The inner body 318 may be considered to be akin to or may be substantially similar to the spring guide 240 shown in FIGS. 2A to 2G and described above in relation thereto. In the example shown, the inner body 318 is hollow and generally cylindrical, although it is envisaged that the inner body 318 may have any other suitable shape or form, for example it may comprise any other suitable generally prismatic shape. The inner body 318 comprises one or more blocking elements 319 configured to engage with and/or interface with the lock ring 304 to obstruct rotational movement of the lock ring 304 about the longitudinal axis 310 relative to the outer body 301, to provide for the first and second states of the lock ring 304. The inner body 318 also comprises one or more stopper portions 320 configured to engage with one or more respective stoppers 326 arranged to protrude radially inwards towards the inner body 318 from an inner surface of the outer body 301; and one or more engagement portions 321 for engaging with the cap 305, such that the inner body 318 may be removably coupled to the cap 305.

Whilst in the examples shown and described herein, the one or more blocking elements 319 are integrally formed with the inner body 318 such that the inner body 318 comprises the one or more blocking elements 319, it is also envisaged that the one or more blocking elements 319 need not necessarily be integrally formed with or coupled to the inner body 318. The one or more blocking elements 319 may have any other suitable form and may be integrally formed with or coupled to any other part of the medicament delivery device 300. For example, the one or more blocking elements 319 may be integrally formed with or coupled to the outer body 301. For example, an inner surface of the outer body 301 configured to interface with the lock ring 304 may comprise one or more blocking elements 319 configured to protrude radially inwards to interface with the lock ring 304 to obstruct its rotational movement, to provide the for the first and second states of the lock ring 304. The one or more blocking elements 319 may be rotationally fixed relative to the outer body 301, such that the lock ring 304 is configured to rotate about the longitudinal axis 310 relative to the one or more blocking elements 319, which remain relatively stationary. Furthermore, in the example shown, there is a single blocking element 319. However, it is envisaged that the medicament delivery device 300 may comprise any number of one or more blocking elements 319, for example one, two, three, four, five, six or more blocking elements 319, which may be spaced apart from one another equally or irregularly around the circumferential direction 331 about the longitudinal axis 310. For example, the medicament delivery device 300 may comprise two blocking elements 319 equally spaced apart from one another such that they are diametrically opposed from one another, and these may be integrally formed with the inner body 318 or the outer body 301 for example.

The medicament delivery device 300 also comprises a plunger 333, which may considered to be akin to or which may be substantially similar to the plunger 223 shown in FIGS. 2A to 2G and described above in relation thereto. The plunger 333 is arranged inside the outer body 301, and at least partially inside the inner body 318. The plunger 333 is configured to be moved along the distal direction 312 to move the needle from the retracted position/pre-use state into the extended position/ready to use state. The plunger 333 is thus configured to place the needle 302 in an injection position for injecting medicament, and is removably couplable to the inner body 318. Moving the actuation member 303 relative to the outer body 301 along the longitudinal axis 310 to actuate the medicament delivery device 300 causes the plunger 333 to become decoupled from the inner body 318 and to be moved along the distal direction 312 relative to the body 301. A biasing member 334, for example a spring, such as a compression spring, is arranged to bias the plunger 333 towards the distal end 309 of the outer body 301, i.e. in the distal direction 312, and is arranged inside the inner body 318. That is, the inner body 318 may be configured to house the biasing member 334, and may thus also be referred to as a spring guide or a spring housing.

In the example shown, moving the actuation member 303 relative to the outer body 301 along the longitudinal axis 310 causes the plunger 333 to become decoupled from the inner body 318 because the inner body 318 comprises an aperture 339 for receiving one or more axially extending deflectable arms 335 of the plunger 333. Each of the one or more arms 335 of the plunger 333 comprises a fixed end 336 and a free end 337 arranged opposite to the fixed end 336. At the free end 337, each arm 335 comprises a clip 338, for example which may be generally triangular or wedge shaped, which is configured to be received in the aperture 339 of the inner body 318 and form a snap fit therewith, to couple the plunger 333 to the inner body 318. Deflection of the deflectable arms 335 relative to the longitudinal axis 310 can cause the arms 335 to deflect inwards to unhook the clips 338 from the aperture 339, such that the clips 338 are no longer in a snap fit arrangement with the aperture 339, such that the plunger 333 may be moved along the distal direction 312 relative to the inner body 318 and decoupled therefrom. The deflectable arms 335 may be caused to deflect and move along the distal direction 312 in this way by applying a force to the plunger 333 along the distal direction by actuating the actuation member 303.

For example, the actuation member 303, which in the example shown is generally cylindrical, may comprise a receiving portion 315 for engagement with the plunger 333. The receiving portion 315 may be generally cylindrical and hollow and arranged to protrude away from the actuation surface 314 into the lock ring 304 and it may be generally coincident with the longitudinal axis 310. The receiving portion 315 may be sized to fit over and/or around the clips 338 of the arms 335 of the plunger 333, such that movement of the actuation member 303 in the distal direction 312 by pressing the actuation member 303, for example from an extended position into a retracted position, to actuate the medicament delivery device 300, causes the receiving portion 315 to push down on, in the distal direction 312, and to circumscribe the clips 338. This causes the clips 338 to be pushed radially inwards towards the longitudinal axis 310, which causes the deflectable arms 335 to be deflected or flexed inwards, to unhook the clips 338 from the aperture 339 of the inner body 318, thus causing the plunger 333 to become decoupled from the inner body 318, to permit the plunger 333 to be moved along the distal direction 312 in order to move the needle 302 into a position for injection. That is, when the plunger 333 is coupled to the inner body 318, the plunger 333 is longitudinally constrained from moving in the distal direction 312 to place the needle 302 into the ready for use, injection position, but the plunger 333 is caused to become decoupled from the inner body 318 by moving the actuation member 303 to actuate the medicament delivery device 300.

Similarly, the cap 305 is configured to form a snap fit with the inner body 318 to removably couple the cap 305 to the inner body 318. The cap 305 comprises one or more axially extending arms 322 which each include a fixed end 323 and a free end 324 opposite to the fixed end 323. In the example shown, the cap 305 comprises two axially extending arms 322 which are diametrically opposed to one another, i.e. a pair of axially extending arms equally spaced apart from one another about the longitudinal axis 310. However, it is envisaged that the cap 305 may comprise any number of one or more axially extending arms 322, for example, one, two, three, four, five, six or more axially extending arms 322, which may be equally or irregularly spaced apart from one another about the longitudinal axis 310.

At the free end 324 of each of the arms 322 there is a clip 325, which may be generally triangular or wedge shaped. Each of the clips 325 is configured to hook onto and/or around a respective one of the engagement portions 321 of the inner body 318, for example as shown in FIG. 3A, in order to form a snap fit therewith to couple the cap 305 to the inner body 318. Thus, when the cap 305 is coupled to the inner body 318, movement of the cap 305 along the longitudinal axis 310 in the distal direction 312 relative to the outer body 301 causes the inner body 318 to also move along the longitudinal axis 310 in the distal direction 312 relative to the outer body 301. However, as shown in FIG. 3B for example, the one or more stopper portions 320 of the inner body 318 are configured to engage with one or more respective stoppers 326 arranged to protrude radially inwards towards the inner body 318 from an inner surface of the outer body 301, meaning that the one or more stopper portions 320 and stoppers 326 serve to limit the range of motion of the inner body 318 along the longitudinal axis 310 in the distal direction 312 by preventing the inner body 318 from moving in the distal direction 312 relative to the outer body 301 beyond the point at which the one or more stopper portions 320 engage with and abut the stoppers 326 and are hence blocked from moving further along the distal direction 312 thereby. Such a position is shown in FIG. 3B for example. Next, as shown sequentially between FIGS. 3B and 3C, as the cap 305 is moved further along the distal direction 312 in order to remove the cap 305 from the outer body 301, because the inner body 318 is longitudinally held in place and is prevented from moving further along the distal direction 312 with the cap 305, the force applied by a user on the cap 305 to pull it further away from the outer body 301 in the distal direction 312 causes the one or more clips 325 to apply a force against the one or more respective engagement portions 321 of the inner body 318 in the distal direction 312, which upon further pulling of the cap 305 in the distal direction 312, causes the one or more clips 325 to become unhooked from the engagement portions 321, and for the one or more axially extending arms 322 to deflect radially outwards away from the longitudinal axis 310. Thus, the cap 305 becomes uncoupled from the inner body 318 and is free to move further along the distal direction 312 relative to the outer body 301, in order to fully remove the cap 305. In other words, during movement of the cap 305 in the distal direction 312 along a first axial range of motion, for example as shown sequentially between FIGS. 3A and 3B, the inner body 318 is coupled to the cap 305 and the blocking element 319 is caused to move from the first position into the second position, and completion of the longitudinal movement of the cap 305 along the first axial range of motion causes the cap 305 to become decoupled from the inner body 318 as shown in FIG. 3C, such that the inner body 318 is decoupled from the cap 305 during movement of the cap 305 in the distal direction 312 along a second axial range of motion, such that as the cap 305 is moved further along the distal direction 312 in the second axial range of motion into the position shown in FIG. 3D for example in which the cap 305 is fully removed, the inner body 318 does not move further along the distal direction 312 together with the cap 305. Completion of the movement of the cap 305 along the first axial range of motion causes the one or more axially extending arms 322 to deflect or flex relative to the inner body 318 in order to permit the cap 305 to become decoupled from the inner body 318.

In this manner, in an initial pre-use state of the medicament delivery device 300, for example as shown in FIG. 3A, the cap 305 is in the capped position and the cap 305 is coupled to the inner body 318 such that movement of the cap 305 along the distal direction 312 will cause the inner body 318 to correspondingly move along the distal direction 312. In this state, the plunger 333 is also coupled to the inner body 318. Further distal movement of the cap 305 will cause the cap 305 to become decoupled from the inner body 318, via deflection of the one or more axially extending arms 322, to permit the cap 305 to be fully removed from the outer body 301. This distal movement of the cap 305 causes the lock ring 304 to be placed into a state in which it is permitted to move rotationally relative to the outer body 301 about the longitudinal axis 310, to permit the actuation member 303 to be moved along the longitudinal axis 310 in order to actuate the medicament delivery device 300. The actuation member 303 can thus then be pressed or depressed for example, to move the actuation member 303 in the distal direction 312, which causes the plunger 333 to become decoupled from the inner body 318, by deflection of the one or more deflectable arms 335. This causes the plunger 333 to be moved along the distal direction 312 to move the needle 302 into an injecting position such that the medicament delivery device 300 is ready to use. The actuation member 303 may only be pressed to actuate the plunger 333 when the lock ring 304 is in the second position in which the actuation member 303 is permitted to move along the longitudinal axis 310 relative to the outer body 301, and the lock ring 304 may only be permitted to be arranged in the second position once the cap 305 has been moved away from the capped position. Examples of how moving the cap 305 in the distal direction 312 away from the distal end 309 of the outer body 301 along the longitudinal axis 310 to decouple the cap 305 from the outer body 301 can cause the lock ring 304 to be in the second state in which the lock ring 304 is permitted to rotate from the first position towards the second position shall now be described below.

In the example shown in FIGS. 3A to 3E, the lock ring 304 comprises a first annular portion 327 and a second annular portion 328 which are arranged along the longitudinal axis 310. In the example shown, the first annular portion 327 and the second annular portion 328 are arranged adjacent to one another along the longitudinal axis 310, such that they abut one another. However, it is also envisaged that the first and second annular portions 327, 328 may be spaced apart from one another along the longitudinal axis 310. The first annular portion 327 is arranged closer to the proximal end 306 of the medicament delivery device 300 than the distal end 307, and the second annular portion 328 is arranged closer to the distal end 307 of the medicament delivery device 300 than the proximal end 306.

A circumferential direction 331 is defined as circumscribing the longitudinal axis 310, and each of the first and second annular portions 327, 328 is arranged to extend along the circumferential direction 331 about the longitudinal axis 310. Each of the first and second annular portions 327, 328 is generally ring shaped. As aforementioned, the inner body 318 comprises one or more blocking elements 319 configured to engage with and/or interface with the lock ring 304 to obstruct rotational movement of the lock ring 304 about the longitudinal axis 310 relative to the outer body 301. In the example shown, the inner body 318 comprises a single blocking element 319 arranged to protrude radially outwards away from the longitudinal axis 310 and towards an inner surface of the outer body 301. The first annular portion 327 comprises a first receiving segment 329 comprising an aperture, channel, recess, groove or cut-out configured to receive the blocking element 319. Similarly, the second annular portion 328 comprises a second receiving segment 330 comprising an aperture, channel, recess, groove or cut-out configured to receive the blocking element 319. When the medicament delivery device 300 is in an initial pre-use state, for example as shown in FIG. 3A, the blocking element 319 is arranged to be longitudinally aligned with the first annular portion 327 along the longitudinal axis 310. When the cap 305 is moved along the distal direction 312 with the inner body 318 coupled thereto, thus causing the inner body 318 to also move along the distal direction 312, then the inner body 318 is pulled along the distal direction 312 such that the blocking element 319 is then arranged to be longitudinally aligned with the second annular portion 328 along the longitudinal axis 310. Thus, moving the cap 305 along the distal direction 312 out from the capped position causes the blocking element 319 to be pulled from the first annular portion 327 to the second annular portion 328, and hence to be pulled out from the first receiving segment 329 and into the second receiving segment 330.

The first receiving segment 329 is arranged to extend around a portion of the circumference of the first annular portion 327, i.e. it does not extend around the entire circumference of the first annular portion 327 along the circumferential direction 331. Similarly, in the example shown, the second receiving segment 330 is arranged to extend around a portion of the circumference of the second annular portion 328, i.e. it does not extend around the entire circumference of the second annular portion 328 along the circumferential direction 331. However, it is envisaged that the second receiving segment 330 may be sized to extend around substantially all of or the entire circumference of the second annular portion 328. In any case, the second receiving segment 330 is arranged to extend around a larger portion of the circumference of the lock ring 304 than the first receiving segment 329. That is, the first receiving segment 329 is arranged to extend around the circumferential direction 331 by a first angle or a first length, and the second receiving segment 330 is arranged to extend around the circumferential direction 331 by a second angle or a second length, wherein the second angle or the second length is larger than the first angle or the first length. Thus, the range of rotational motion of the lock ring 304 about the longitudinal axis 310 relative to the outer body 301 is larger when the blocking element 319 is received in the second annular portion 328 of the lock ring 304 than when the blocking element 319 is received in the first annular portion 327 of the lock ring 304. The first receiving segment 329 may even be sized to be approximately the same size as the blocking element 319 which no space or gap therein, to prevent any rotational movement of the lock ring 304 at all when the blocking element 319 is received in the first receiving segment 329. In any case, pulling the cap 305 in the distal direction 312, causing the blocking element 319 to be pulled down in the distal direction 312 from the first receiving segment 329 into the second receiving segment 330, causes the lock ring 304 to be permitted to rotate about the longitudinal axis 310 relative to the outer body 301 from the first position into the second position. That is, when the blocking element 319 is received in the first receiving segment 329 the lock ring 304 is in the first state in which the lock ring 304 is in the first position and is not permitted to rotate towards the second position, and when the blocking element 319 is received in the second receiving segment 330 the lock ring 304 is in the second state in which it is permitted to rotate from the first position towards the second position.

Figures 4A, 4B:
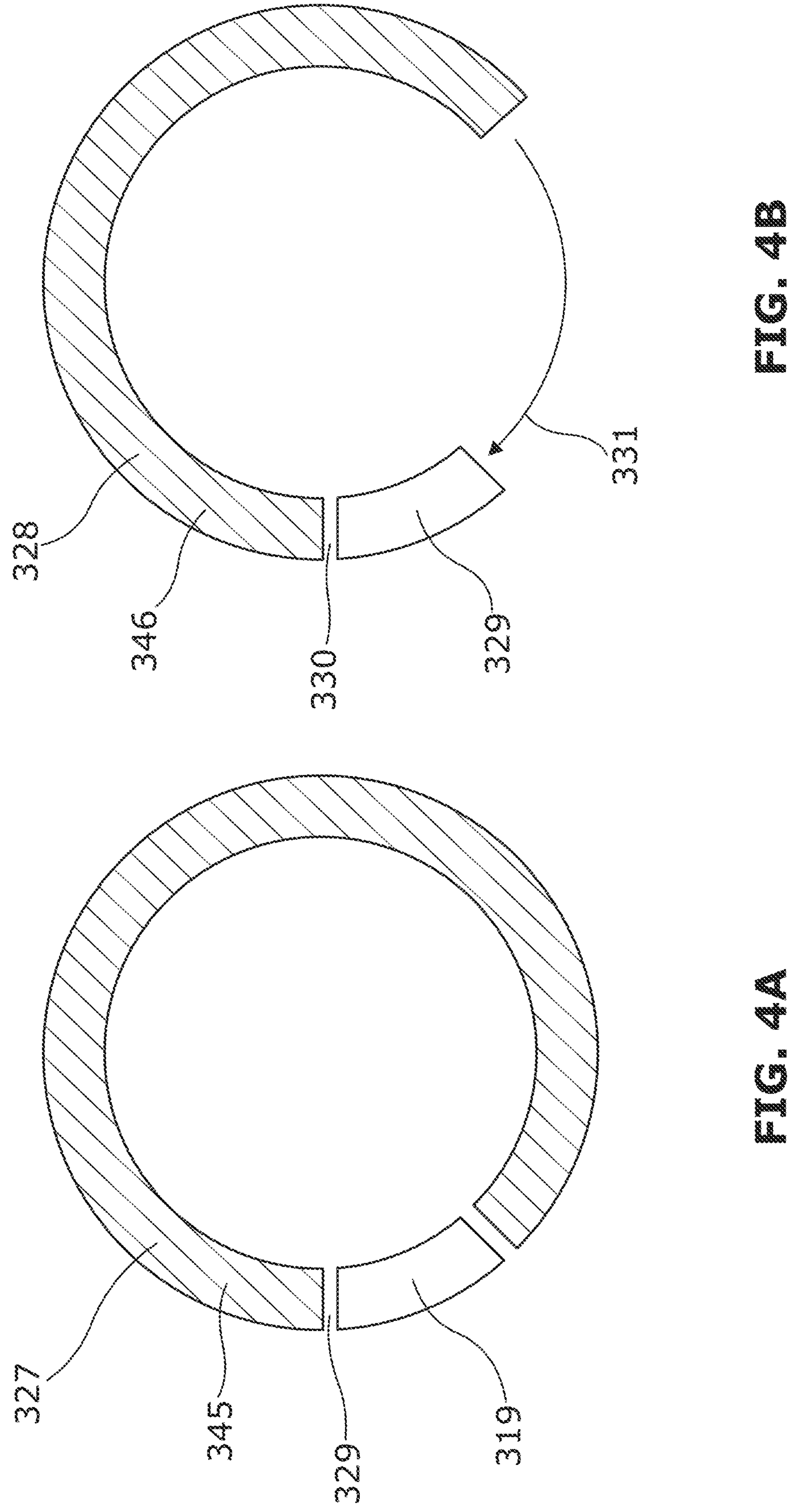
FIG. 4A shows a cross-sectional schematic view of a first annular portion of a lock ring.
FIG. 4B shows a cross-sectional schematic view of a second annular portion of a lock ring.

Referring now to the cross-sectional schematic FIGS. 4A and 4B, the second annular portion 328 is configured to permit rotation of the lock ring 304 from the first position towards the second position, and the first annular portion 327 is configured to not permit rotation of the lock ring 304 towards the second position, by means of the first and second annular portions 327, 328 comprising first and second blocking segments 345, 346 respectively. That is, in the remainder of the first annular portion 327 which does not comprise the first receiving segment 329, the first annular portion 327 comprises a first blocking segment 345, which is generally solid and is configured to engage with the blocking element 319. The first receiving segment 329 extends around a first portion of the circumference of the first annular portion 327, and the first blocking segment 345 extends around the remainder of the circumference of the first annular portion 327. Similarly, in the remainder of the second annular portion 328 which does not comprise the second receiving segment 330, the second annular portion 328 comprises a second blocking segment 346, which is generally solid and is configured to engage with the blocking element 319. The second receiving segment 330 extends around a first portion of the circumference of the second annular portion 328, and the second blocking segment 346 extends around the remainder of the circumference of the second annular portion 328.

In the example shown, the blocking element 319 is sized to be approximately the same size in the circumferential direction 331 as the first receiving segment 329. Thus, when the blocking element 319 is received in the first receiving segment 329, the lock ring 304 is prevented from rotating towards the second position, whereas when the blocking element 319 is received in the second receiving segment 330, which is sized to be larger than the blocking element 319, the lock ring 304 is permitted to rotate relative to the blocking element 319 about the longitudinal axis 310 and relative to the outer body 301 along the circumferential direction 331 as shown in FIG. 4B. Thus, the medicament delivery device 300 may be prepared for use prior to dispensing medicament as described below with reference to FIGS. 3A to 3E. It is envisaged that the first and second annular portions 327, 328 may have any other suitable shape or form in order to provide that when the blocking element 319 is aligned with the first annular portion 327, the lock ring 304 is in the first state and is not permitted to rotate from the first position towards the second position, and when the blocking element 319 is aligned with the second annular portion 328, the lock ring 304 is in the second state and is permitted to rotate from the first position towards the second position.

FIG. 3A shows the medicament delivery device 300 in a pre-use state in which the cap 305 is in the capped position. To prepare the medicament delivery device 300 for use, a user may remove the cap 305 by pulling it away from the outer body 301 along the distal direction 312, such that the contact surface 343 is brought out of contact with to be spaced apart from the contact surface 344, as shown in FIG. 3B. Because the one or more axially extending arms 322 of the cap 305 are coupled to the one or more engagement portions 321 of the inner body 318, this pulls the inner body 318 along the distal direction 321, which causes the blocking element 319 to be moved out from the first receiving segment 329 in which the lock ring 304 is not permitted to rotate towards the second position into the second receiving segment 330 in which the lock ring 304 is permitted to rotate from the first position towards the second position. As shown in FIG. 3C, pulling the cap 305 further along the distal direction causes the one or more axially extending deflectable arms 322 to deflect such that the cap 305 becomes decoupled from the inner body 318. The inner body 318 is prevented from moving further along the distal direction 312 by the one or more engagement portions 321 and stoppers 326, but the cap 305 is permitted to be moved further along the distal direction 305 to fully remove it and decouple it from the outer body 301, into the position shown in FIG. 3D in which the cap 305 is removed and is not shown. Next, because the blocking element 319 is now arranged in the second receiving segment 330, the lock ring 304 is free to be rotated from the first position towards the second position. A user may then rotate the lock ring 304 about the longitudinal axis 310 relative to the outer body 301. As described above, this permits the actuation member 303 to be moved along the longitudinal axis 310 relative to the outer body 301. The user may then press the actuation member 303 to move it along the distal direction 312, which causes the plunger 333 to become decoupled from the inner body 318 by the receiving portion 315 engaging with the one or more clips 338 to deflect the one or more arms 335 of the plunger 333, causing the plunger 333 to move along the distal direction 312 to place the needle 302 in the extended position in which it is ready to use to deliver medicament. The actuation member 303 may be biased back towards the extended, proximal position, by a biasing member such as a spring (not shown), such that upon removal of a user applied force to the actuation surface 314, the actuation member 303 is caused to move back to the extended position along the proximal direction 313, into the position shown in the example of FIG. 3E.

FIGS. 5A to 5D show another exemplary medicament delivery device 300 in which like reference numerals denote like elements as shown in FIGS. 3A to 3E and as described above. The medicament delivery device 300 of FIGS. 5A to 5D differs from that shown in FIGS. 3A to 3E and described above in that rather than the lock ring 304 comprising first and second annular portions 327, 328 comprising first and second receiving segments 329, 330 respectively for receiving the blocking element 319, the lock ring 304 instead comprises an inclined surface 332. Between the proximal end 306 and the distal end 307 of the medicament delivery device 300, i.e. along the distal direction 312, the inclined surface 332 is angled downwards, that is, the inclined surface 332 is angled towards the distal end 307. The inclined surface 332 is angled relative to the circumferential direction 331. In the example shown, the inclined surface 332 is generally straight and linear, however it is envisaged that the inclined surface 332 need not necessarily be generally straight and linear and that it may comprise one or more curved portions, for example, the inclined surface 332 may be generally curved along its entire length. The inclined surface 332 is configured to move relative to the blocking element 319, such that the blocking element 319 engages with and relatively moves along the inclined surface 332, which forces the lock ring 304 to rotate about the longitudinal axis 310.

This movement shall now be described in more detail with reference to the simplified schematic representation of FIG. 6 which shows an exemplary inclined surface 332 and the blocking element 319. As the cap 305 is moved along the distal direction 312, thus pulling the inner body 318 along the distal direction 312 with it, this causes the blocking element 319 of the inner body 318 to be moved along the distal direction 312. Because the blocking element 319 bears against the inclined surface 332 of the lock ring 304, this causes the blocking element 319 to move relative to the inclined surface 332 along the inclined surface 332 in the direction shown by the arrow 347 in FIG. 6. However, since the blocking element 319 is rotationally fixed about the longitudinal axis 310 relative to the outer body 301, but it is the lock ring 304 that is configured to be rotatable about the longitudinal axis 310 relative to the outer body 301, this relative movement is actually realised by the lock ring 304 moving relative to the blocking element 319. That is, the blocking element 319 remains relatively fixed, whilst the inclined surface 332 of the lock ring 304 moves relative to the blocking element 319. Thus, this downwards movement of the blocking element 319 along the distal direction 312, because the blocking element 319 cannot rotate about the longitudinal axis 310, causes the lock ring 304 to rotate about the longitudinal axis 310 relative to the blocking element 319 and the outer body 201 along the circumferential direction 331, which in the example shown in FIG. 6 is an anticlockwise circumferential direction. In this manner, longitudinal movement of the blocking element 319 along the distal direction 312 is converted to automatic rotational movement of the lock ring 304 about the longitudinal axis 310. Thus, the act of removing the cap 305 from the capped position and moving it along the distal direction 312 automatically causes the lock ring 304 to be rotated from the first position to the second position, without a user having to manually rotate the lock ring 304 into the second position themselves, such that the medicament delivery device 300 is automatically prepared to be ready for use upon removal of the cap 305, wherein the actuation member 303 is permitted to move along the longitudinal axis 310 relative to the outer body 301 to actuate the medicament delivery device 300. Accordingly, the medicament delivery device 300 may be prepared for use prior to dispensing medicament as described below with reference to FIGS. 5A to 5D.

Figures 5A, 5B:
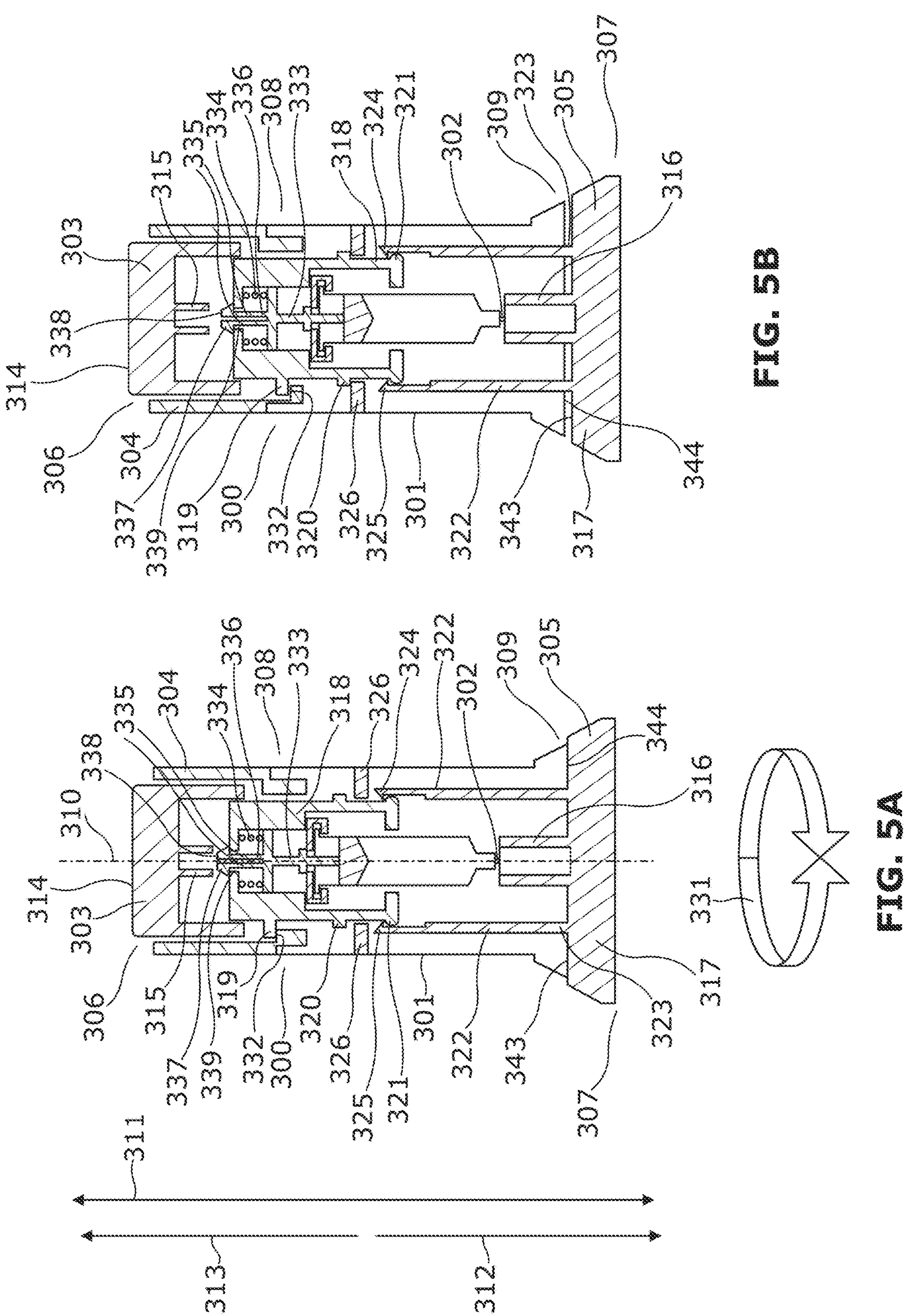
FIG. 5A shows a cross-sectional schematic view of a medicament delivery device with the cap in a capped position.
FIG. 5B shows a cross-sectional schematic view of a medicament delivery device with the cap in an intermediate position.
Figure 5D:
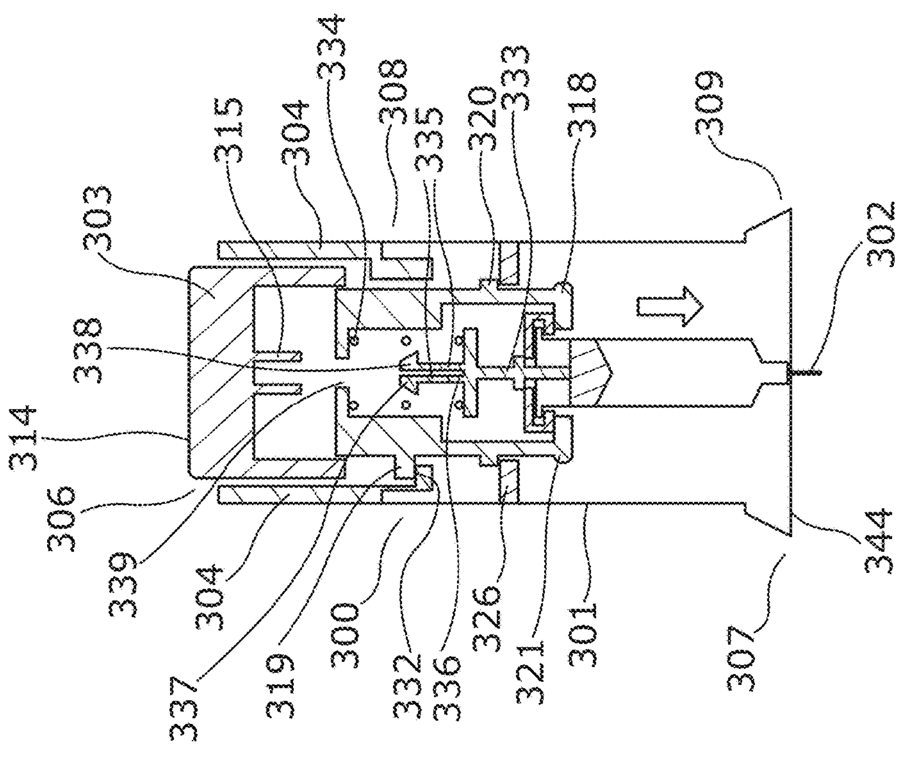
FIG. 5D shows a cross-sectional schematic view of a medicament delivery device with the cap removed and in a ready for use state.
Figure 5C:
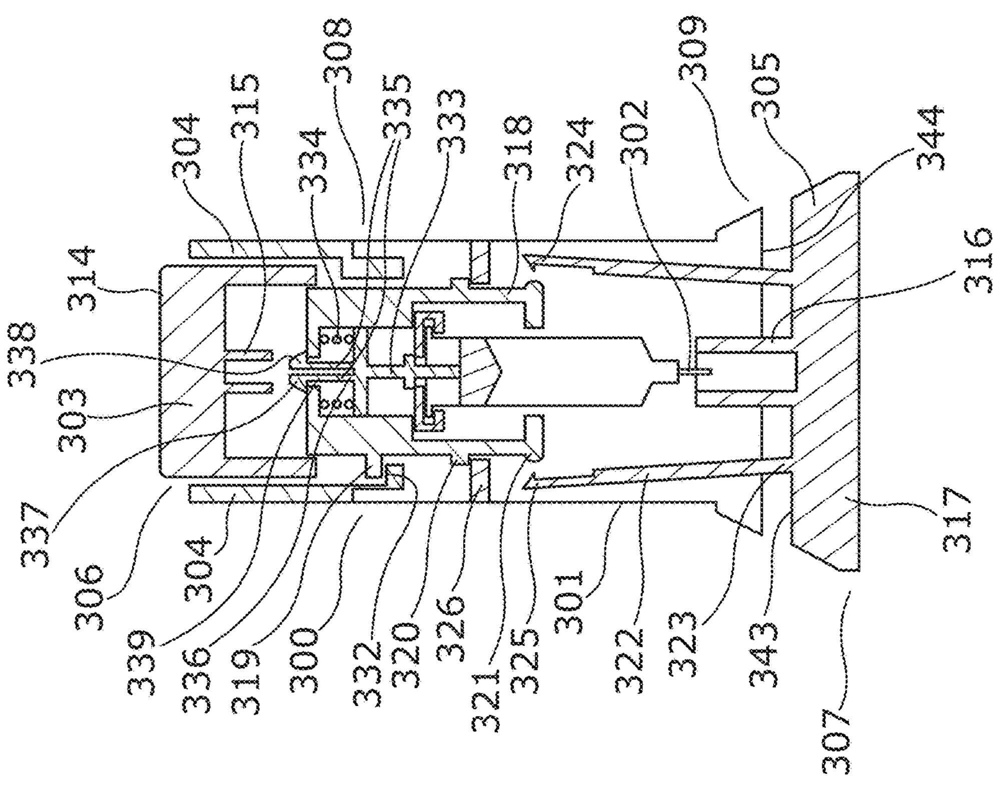
FIG. 5C shows a cross-sectional schematic view of a medicament delivery device with the cap in an intermediate position.
Figure 6:
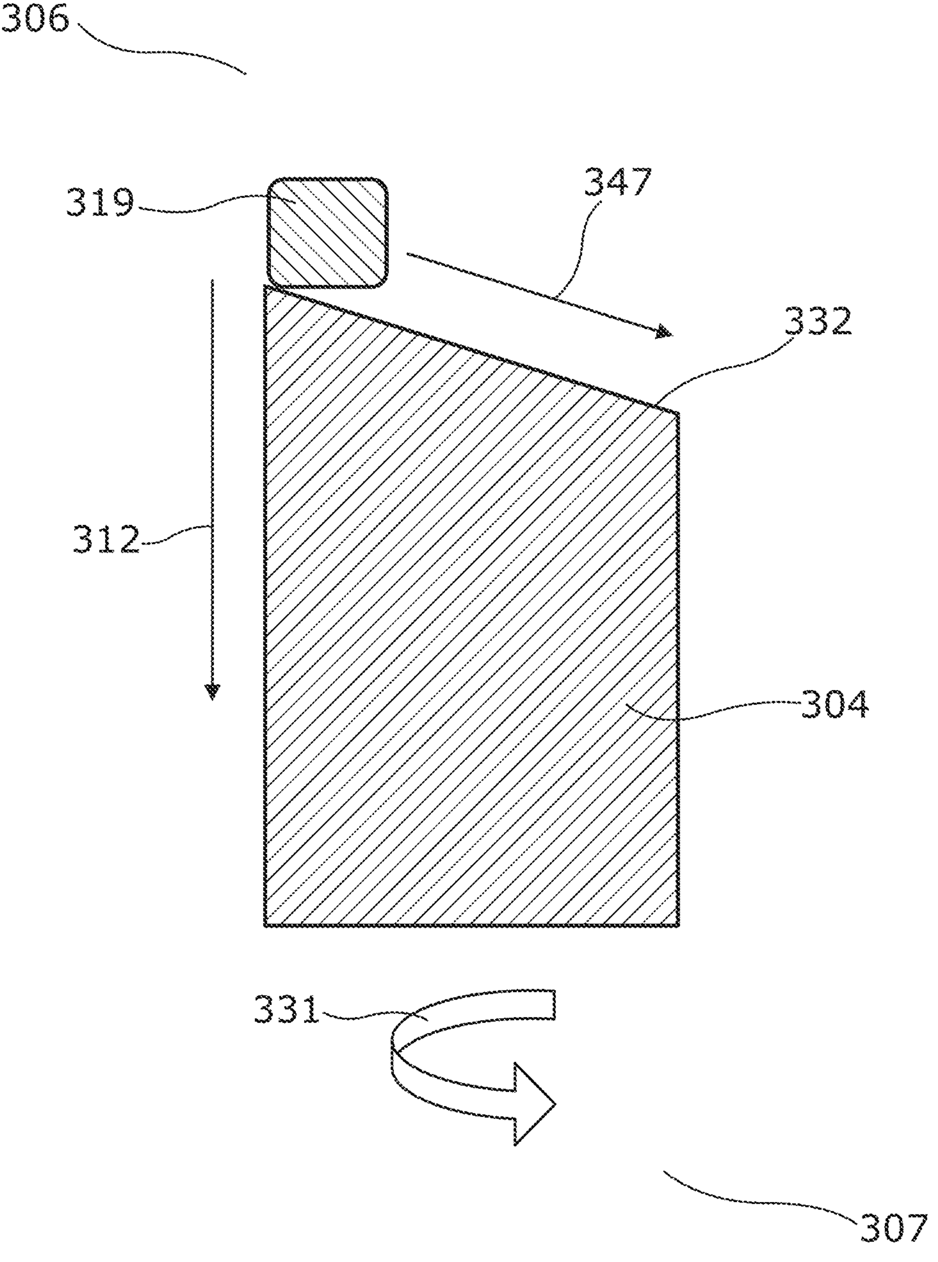
FIG. 6 shows a schematic view of a blocking element and an inclined surface of a lock ring.

FIG. 5A shows the medicament delivery device 300 in a pre-use state in which the cap 305 is in the capped position. To prepare the medicament delivery device 300 for use, a user may remove the cap 305 by pulling it away from the outer body 301 along the distal direction 312, such that the contact surface 343 is brought out of contact with to be spaced apart from the contact surface 344, as shown in FIG. 5B. Because the one or more axially extending arms 322 of the cap 305 are coupled to the one or more engagement portions 321 of the inner body 318, this pulls the inner body 318 along the distal direction 312, which causes the blocking element 319 to be moved along the distal direction 312, thus causing relative movement between the blocking element 319 and the inclined surface 332, which converts the longitudinal movement of the blocking element 319 into rotational movement of the lock ring 304. The lock ring is thus caused to rotate from the first position as shown in FIG. 5A towards the second position as shown in FIG. 5B. As shown in FIG. 5C, pulling the cap 305 further along the distal direction causes the one or more axially extending deflectable arms 322 to deflect such that the cap 305 becomes decoupled from the inner body 318. The inner body 318 is prevented from moving further along the distal direction 312 by the one or more engagement portions 321 and stoppers 326, but the cap 305 is permitted to be moved further along the distal direction 305 to fully remove it and decouple it from the outer body 301, into the position shown in FIG. 5D in which the cap 305 is removed and is not shown. Next, because the lock ring 304 has been rotated into the second position in which the actuation member 303 is permitted to be moved along the longitudinal axis 310 relative to the outer body 301, the user may then press the actuation member 303 to move it along the distal direction 312, which causes the plunger 333 to become decoupled from the inner body 318 by the receiving portion 315 engaging with the one or more clips 338 to deflect the one or more arms 335 of the plunger 333, causing the plunger 333 to move along the distal direction 312 to place the needle 302 in the extended position in which it is ready to use to deliver medicament. The actuation member 303 may be biased back towards the extended, proximal position, by a biasing member such as a spring (not shown), such that upon removal of a user applied force to the actuation surface 314, the actuation member 303 is caused to automatically move back to the extended position along the proximal direction 313, into the position shown in the example of FIG. 5D.

Figures 7A, 7B:
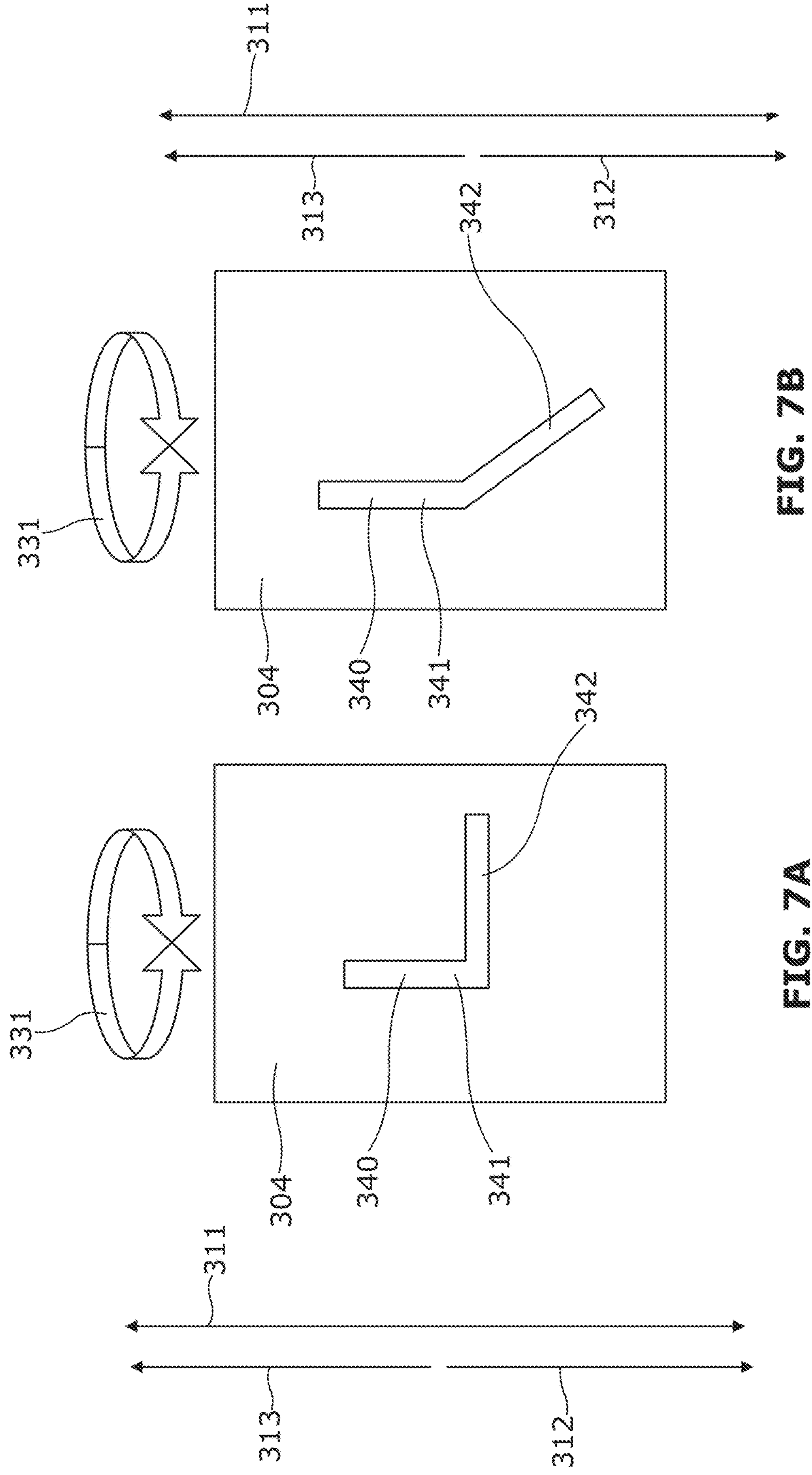
FIG. 7A shows a schematic side view of a lock ring comprising a receiving element.
FIG. 7B shows a schematic side view of a lock ring comprising a receiving element.

FIGS. 7A and 7B show other examples of lock rings 304 which may be employed in the exemplary medicament delivery devices 300 shown in the preceding figures and described above, and in other medicament delivery devices too. In the example shown in FIG. 7A, the lock ring 304 comprises a receiving element 340 comprising a slot 340 configured to receive the blocking element 319. It is also envisaged that the receiving element 340 may comprise a groove, a channel, an aperture or a cut-out configured to receive the blocking element 319. The slot 340 comprises a first portion 341 extending generally parallel to the longitudinal axis 310 and the longitudinal direction 311, and a second portion 342 extending generally along the circumferential direction 331, such that the second portion 342 is generally perpendicular to the second portion 342 and is arranged to extend circumferentially about the longitudinal axis 310. Thus, initially, the blocking element 319 is configured to be arranged at an upper proximal end of the first portion 341 of the slot 340, in which the blocking element 319 is permitted to move relative to the slot 340 and hence relative to the lock ring 304 only in the distal direction 312 and not circumferentially or rotationally. Moving the cap 305 along the distal direction 312 causes the blocking element 319 to move along the distal direction 312 along the first portion 341 of the slot 340, such that the blocking element 319 is then arranged at a lower distal end of the first portion 341 of the slot 340 where the first portion 341 joins with the second portion 342. Because the second portion 342 extends generally in the circumferential direction 331, this then permits relative movement between the blocking element 319 and the second portion 342 of the slot 340 to allow the lock ring 304 to rotate in the circumferential direction 331 about the longitudinal axis 310 relative to the outer body 301 and the blocking element 319. Hence, longitudinal movement of the blocking element 319 along the distal direction 312 is converted into rotational movement of the lock ring 304, to cause or permit the lock ring 304 to be rotated from the first position into the second position.

The example of FIG. 7B differs from that of FIG. 7A in that the second portion 342 of the slot 340 is inclined, i.e. angled, relative to the circumferential direction 331, to provide for more gradual conversation of the longitudinal movement of the blocking element 319 along the distal direction 312 into rotational movement of the lock ring 304. It is envisaged that the slot 340 may have any other suitable shape or form, for example the slot 340 may comprise one or more additional portions in addition to the first and second portions 341, 342, and/or one or more of the portions 341, 342 of the slot 340 need not necessarily be generally straight and linear but may be at least partially curved. One or more of the features of the exemplary lock rings 304 of FIGS. 7A and 7B may be combined with the examples of FIGS. 3A to 3E and 5A to 5D as described above. For example, in the example of FIGS. 5A to 5D, the inclined surface 332 may comprise the second portion 342 of the slot 340 of the example of FIG. 7B, and the lock ring 304 may additionally comprise a receiving element portion 341 that is oriented generally parallel to the longitudinal axis 310 and is angled relative to the inclined surface 332, such that initially, when the cap 305 is in the capped position and has not yet been moved along the distal direction 312, the blocking element 319 is constrained to relative movement within the generally longitudinal first portion 341, which initially prevents the lock ring 304 from being rotatable, until the blocking element 319 is moved further in the distal direction 312 to be aligned with and received in the second portion 342, for relative movement along the inclined surface 332.

Figure 8:
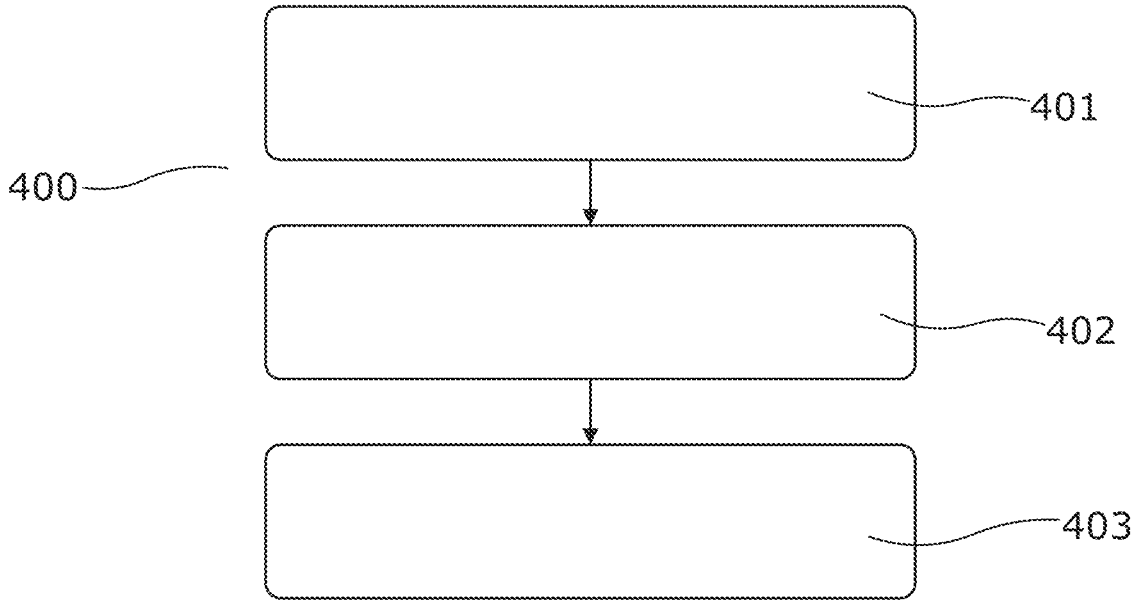
FIG. 8 shows a flowchart illustrating a method of preparing a medicament delivery device for use prior to dispensing medicament from the medicament delivery device.

FIG. 8 shows a flowchart depicting a method 400 of preparing a medicament delivery device 300 for use prior to dispensing medicament from the medicament delivery device 300. The method 400 comprises steps 401, 402 and 403. Step 401 comprises removing the cap 305 from the outer body 301 by moving it from the capped position along the distal direction 312. Step 402 comprises moving the lock ring 304 from the first position to the second position, by rotating the lock ring 304 about the longitudinal axis 310 relative to the outer body 301. The occurrence of step 401 permits step 402 to occur. That is, when the cap 305 is in the capped position, the lock ring 304 is in a first state in which the lock ring 304 is in the aforementioned first position and is not permitted to rotate towards the aforementioned second position. Then, the occurrence of step 401, that is moving the cap 305 in the distal direction 312 to decouple the cap 305 from the outer body 301, causes the lock ring 304 to be in a second state in which the lock ring 304 is permitted to rotate from the first position towards the second position. Step 402 may be performed manually after step 401, for example by a user rotating the lock ring 304 relative the outer body 301, or step 402 may occur automatically, thus negating the need for a user to manually rotate the lock ring 304. Step 402 may automatically occur at least partially simultaneously with step 401, or step 402 may automatically occur subsequently after step 401. Next, step 403 comprises moving the actuation member 303 along the longitudinal axis 310 to actuate the medicament delivery device 300. Step 403 may for example comprise moving the actuation member 303 in the distal direction 312 from an extended, presented position, into a retracted, depressed position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (SIRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms “analogue” and “derivative” refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as “insulin receptor ligands”. In particular, the term “derivative” refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term “antibody”, as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms “fragment” or “antibody fragment” refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302).

For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014 (E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

An example of a compound to be administered with the drug delivery device disclosed herein is a compound with the INN tirzepatide, as referenced in claim 1 of U.S. Pat. No. 9,474,780.

An example of a pharmaceutical composition to be administered with the drug delivery device disclosed herein is a pharmaceutical composition as referenced in U.S. Pat. No. 11,357,820.

An example of a pharmaceutical composition to be administered with the drug delivery device disclosed herein includes a 0.5 mL solution of 2.5 mg, 5 mg, 7.5 mg, 10 mg, 12.5 mg, or 15 mg of tirzepatide and the following excipients sodium chloride (4.1 mg), sodium phosphate dibasic heptahydrate (0.7 mg), and water for injection. Hydrochloric acid solution and/or sodium hydroxide solution may be added to adjust the pH.

An example starting dosage tirzepatide may be 2.5 mg injected subcutaneously once weekly. After four weeks, the tirzepatide dosage may be increased to 5 mg injected subcutaneously once weekly. The dosage may be further increased in 2.5 mg increments after at least four weeks on the current dose. In an example, the maximum dosage of tirzepatide may be 15 mg injected subcutaneously once weekly. If a dose is missed, patients may be instructed to administer tirzepatide as soon as possible within four days (96 hours) after the missed dose. If more than four days have passed, patients may skip the missed dose and administer the next dose on the regularly scheduled day. In each case, patients may then resume their regular once weekly dosing schedule. The day of weekly administration may be changed, if necessary. The time between two doses may be at least three days (72 hours).

Tirzepatide dosages may include 2.5 mg/0.5 mL, 5 mg/0.5 mL, 7.5 mg/0.5 mL, 10 mg/0.5 mL, 12.5 mg/0.5 mL, and 15 mg/0.5 mL. Tirzepatide may be stored in a refrigerator at 2° C. to 8° C. (36° F. to 46° F.). A single-dose pen or single-dose vial may be stored unrefrigerated at temperatures not to exceed 30° C. (86° F.) for up to 21 days. Tirzepatide may be stored in a carton.

Those of skill in the art will understand that modifications (additions and/or removals) of various components of the embodiments described herein may be made without departing from the full scope and spirit of the present invention, which encompass such modifications and any and all equivalents thereof.

REFERENCE NUMERALS

10—device
11—housing
12—cap
13—needle sleeve
17—needle
20—distal region
21—proximal region
22—button
23—piston
200—medicament delivery device
201—body
202—distal end of the body
208—locking member
216—lock ring
217—needle
223—plunger
227—actuation member
228—button
229—dispensing mechanism
232—injection site
240—spring guide
242—protrusions
250—syringe
254—cap
258—stop
260—spring
262—spring
264—clip
265—proximal opening
266—needle shield
267—first collar
268—second collar
300—medicament delivery device
301—outer body
302—needle
303—actuation member
304—lock ring
305—cap
306—proximal end of device
307—distal end of device
308—proximal end of outer body
309—distal end of outer body
310—longitudinal axis
311—longitudinal direction
312—distal direction
313—proximal direction
314—actuation surface of button
315—receiving portion of button
316—needle shield portion of cap
317—main body portion of cap
318—inner body
319—blocking element
320—stopper portions of inner body
321—engagement portions of inner body
322—axially extending arm of cap
323—fixed end
324—free end
325—clip
326—stopper
327—first annular portion
328—second annular portion
329—first receiving segment
330—second receiving segment
331—circumferential direction
332—inclined surface of lock ring
333—plunger
334—biasing member
335—deflectable arms of plunger
336—fixed end of plunger arm
337—Free end of plunger arm
338—Clip of free end of plunger arm
339—Aperture of inner body for coupling to the plunger
340—Slot in lock ring
341—First portion of slot
342—Second portion of slot
343—contact surface of cap
344—contact surface of body
345—first blocking segment
346—second blocking segment
347—direction of movement of blocking element along inclined surface
400—method
401—method step
402—method step
403—method step

The invention claimed is:

1. A medicament delivery device comprising:

a body comprising a proximal end and a distal end defining a longitudinal axis;

a needle for injecting medicament;

an actuation member moveable relative to the body along the longitudinal axis for actuating the medicament delivery device;

a lock ring configured to rotate relative to the body about the longitudinal axis between a first position in which the actuation member is not permitted to move along the longitudinal axis relative to the body, and a second position in which the actuation member is permitted to move along the longitudinal axis relative to the body; and a cap arrangeable in a capped position in which the cap abuts with and conceals the distal end of the body to conceal the needle;

wherein the medicament delivery device is configured such that (i) when the cap is in the capped position, the lock ring is in a first state in which the lock ring is in the first position and is not permitted to rotate towards the second position, and (ii) moving the cap in a distal direction away from the distal end of the body along the longitudinal axis away from the capped position causes the lock ring to be in a second state in which the lock ring is permitted to rotate from the first position towards the second position.

2. The medicament delivery device of claim 1, wherein the medicament delivery device is configured such that when the lock ring is in the first state the lock ring is not permitted to rotate about the longitudinal axis relative to the body, and when the lock ring is in the second state the lock ring is permitted to rotate about the longitudinal axis relative to the body.

3. The medicament delivery device of claim 1, wherein the actuation member is moveable relative to the body along the longitudinal axis in the distal direction from the first position, to the second position for dispensing medicament from the needle.

4. The medicament delivery device of claim 3, wherein the medicament delivery device further comprises a first biasing member configured to bias the actuation member towards the first position.

5. The medicament delivery device of claim 3, wherein the needle is moveable along the longitudinal axis relative to the body between: a retracted position in which the needle is arranged inside the body, and an extended position for delivering medicament in which at least a portion of the needle protrudes from the distal end of the body, and wherein the medicament delivery device is configured such that moving the actuation member from the first position to the second position along the distal direction causes the needle to be moved from the retracted position to the extended position.

6. The medicament delivery device of claim 1, wherein the medicament delivery device further comprises a blocking element configured to obstruct rotational movement of the lock ring about the longitudinal axis relative to the body; wherein the blocking element is arrangeable in a first position in which the lock ring is in the first state, and a second position in which the lock ring is in the second state; wherein the medicament delivery device is configured such that moving the cap along the distal direction causes the blocking element to move from the first position to the second position.

7. The medicament delivery device of claim 6, wherein the medicament delivery device is configured such that moving the blocking element from the first position to the second position comprises moving the blocking element along the longitudinal axis relative to the body in the distal direction.

8. The medicament delivery device of claim 6, wherein the body is an outer body and the medicament delivery device further comprises an inner body comprising the blocking element and arranged inside the outer body and moveable relative thereto along the longitudinal axis; wherein the inner body is removably couplable to the cap such that when the cap is in the capped position the inner body is coupled to the cap such that movement of the cap in the distal direction causes the inner body to move relative to the outer body along the distal direction together with the cap.

9. The medicament delivery device of claim 8, wherein the medicament delivery device is configured such that during movement of the cap in the distal direction along a first axial range of motion the inner body is coupled to the cap and the blocking element is caused to move from the first position into the second position, and completion of the movement of the cap along the first axial range of motion causes the cap to become decoupled from the inner body, such that the inner body is decoupled from the cap during movement of the cap in the distal direction along a subsequent second axial range of motion.

10. The medicament delivery device of claim 9, wherein the cap comprises one or more arms extending generally parallel to the longitudinal axis and each comprising a clip configured to form a snap fit with the inner body to couple the inner body to the cap; wherein the medicament delivery device is configured such that completion of the movement of the cap along the first axial range of motion causes the one or more arms to deflect or flex relative to the inner body to decouple the cap from the inner body.

11. The medicament delivery device of claim 8, wherein the medicament delivery device further comprises one or more stoppers configured to limit an axial range of motion of the inner body relative to the outer body along the longitudinal axis.

12. The medicament delivery device of claim 8, wherein the medicament delivery device further comprises:

a plunger removably couplable to the inner body and configured to place the needle in an injection position for injecting medicament, wherein moving the actuation member relative to the outer body along the longitudinal axis to actuate the medicament delivery device causes the plunger to become decoupled from the inner body and to move along the distal direction; and a second biasing member configured to bias the plunger towards the distal end of the body, wherein the second biasing member is arranged inside the inner body.

13. The medicament delivery device of claim 12, wherein the plunger comprises one or more deflectable arms each comprising a clip configured to be received in an aperture of the inner body to couple the plunger to the inner body, and wherein the medicament delivery device is configured such that moving the actuation member in the distal direction causes each of the one or more deflectable arms to deflect relative to the longitudinal axis to cause the clip to be moved out from the aperture to permit the plunger to move relative to the inner body along the distal direction.

14. The medicament delivery device of claim 6, wherein the blocking element comprises a radially protruding element configured to be received in a receiving segment of the lock ring when the blocking element is in the second position, to permit the lock ring to rotate relative to the blocking element about the longitudinal axis.

15. The medicament delivery device of claim 6, wherein the lock ring comprises a first annular portion and a second annular portion arranged along the longitudinal axis; wherein the first annular portion comprises a first receiving segment configured to receive the blocking element and which extends around a first portion of the circumference of the lock ring; wherein the second annular portion comprises a second receiving segment configured to receive the blocking element and which extends around a second portion of the circumference of the lock ring; wherein each of the first and second receiving segments comprises an aperture, recess, channel, groove or cut-out; and wherein the second portion is larger than the first portion, such that when the blocking element is received in the first receiving segment the blocking element is in the first position and when the blocking element is received in the second receiving segment the blocking element is in the second position.

16. The medicament delivery device of claim 6, wherein the medicament delivery device is configured such that movement of the blocking element along the longitudinal axis causes the lock ring to rotate about the longitudinal axis.

17. The medicament delivery device of claim 6, wherein the lock ring comprises an inclined surface that is angled relative to a circumferential direction of the lock ring which circumscribes the longitudinal axis, wherein the blocking element is configured to engage with the inclined surface, such that movement of the blocking element along the longitudinal axis causes the inclined surface to move relative to the blocking element to cause the lock ring to rotate about the longitudinal axis.

18. The medicament delivery device of claim 6, wherein the lock ring comprises a receiving element comprising a slot, a groove, a channel, an aperture or a cut-out configured to receive the blocking element; wherein the receiving element comprises a first portion extending generally parallel to the longitudinal axis, and a second portion extending generally along a circumferential direction which circumscribes the longitudinal axis and/or extending at an angle relative to said circumferential direction.

19. The medicament delivery device of claim 1, wherein the medicament delivery device is configured such that moving the cap in the distal direction away from the capped position causes the lock ring to rotate from the first position towards the second position.

20. The medicament delivery device of claim 1, wherein the medicament delivery device contains a medicament.

* * * * *